US010878564B2

(12) United States Patent
Oved

(10) Patent No.: US 10,878,564 B2
(45) Date of Patent: Dec. 29, 2020

(54) SYSTEMS AND METHODS FOR PROCESSING 3D ANATOMICAL VOLUMES BASED ON LOCALIZATION OF 2D SLICES THEREOF

(71) Applicant: Zebra Medical Vision Ltd., Shefayim (IL)

(72) Inventor: Amit Oved, Givatayim (IL)

(73) Assignee: Zebra Medical Vision Ltd., Shefayim (IL)

( * ) Notice: Subject to any disclaimer, the term of this patent is extended or adjusted under 35 U.S.C. 154(b) by 71 days.

(21) Appl. No.: 16/382,235

(22) Filed: Apr. 12, 2019

(65) Prior Publication Data

US 2020/0327661 A1   Oct. 15, 2020

(51) Int. Cl.
  *G06T 7/00* (2017.01)
  *G16H 30/40* (2018.01)
  *G16H 30/20* (2018.01)

(52) U.S. Cl.
  CPC .......... *G06T 7/0012* (2013.01); *G16H 30/20* (2018.01); *G16H 30/40* (2018.01); *G06T 2207/10081* (2013.01)

(58) Field of Classification Search
  CPC ...... A61B 2090/374; A61B 2090/3762; A61B 17/1703; G06T 2207/10081; G06T 7/0012
  See application file for complete search history.

(56) References Cited

U.S. PATENT DOCUMENTS

| 7,800,367 B2* | 9/2010 | Bhardwaj | G01R 33/5615 324/309 |
| 7,893,938 B2* | 2/2011 | Aharon | A61B 5/055 345/422 |
| 7,920,150 B2* | 4/2011 | Ku | G06T 3/40 345/660 |
| 7,920,911 B2* | 4/2011 | Hoshino | G01R 33/287 600/423 |
| 8,019,042 B2* | 9/2011 | Shukla | G06T 7/0016 378/65 |

(Continued)

OTHER PUBLICATIONS

Emrich et al. "CT Slice Localization via Instance-Based Regression", Medical Imaging: Image Processing, Proceedings of the SPIE, 7623: 762320-1-762320-12, Mar. 12, 2010.

(Continued)

*Primary Examiner* — Yosef Kassa

(57) ABSTRACT

There is provided a computer implemented method for localizing target anatomical regions of interest (ROI) of a target individual, comprising: uniformly sub-sampling a plurality of 2D images having sequential index numbers within a 3D anatomical volume, feeding the plurality of sampled 2D images into a classifier for outputting a plurality of values on a normalized anatomical scale, fitting a linear model to the plurality of values and corresponding sequential index numbers, mapping by the linear model, the plurality of 2D images to the normalized anatomical scale, receiving an indication of at least one target anatomical ROI of a target individual, wherein each target anatomical ROI is mapped to the normalized anatomical scale, and providing a sub-set of the plurality of 2D images having values of the normalized anatomical scale corresponding to the received at least one target anatomical ROI.

21 Claims, 11 Drawing Sheets

(56) References Cited

U.S. PATENT DOCUMENTS

| | | | | |
|---|---|---|---|---|
| 8,422,756 | B2* | 4/2013 | Haacke | G01R 33/443 382/131 |
| 8,886,283 | B1* | 11/2014 | Chen | A61B 5/055 600/410 |

OTHER PUBLICATIONS

Feulner et al. "Estimating the Body Portion of CT Volumes by Matching Histograms of Visual Words", Medical Imaging: Image Processing, Proceedings of the SPIE, 7259: 72591V-1-72591V-8, Mar. 27, 2009.

Fischler et al. "Random Sample Consensus: A Paradigm for Model Fitting With Applications to Image Analysis and Automated Cartography", Communications of the ACM, 24(6): 381-395, Jun. 1981.

Graf et al. "2D Image Registration in CT Images Using Radial Image Descriptors", Proceedings of the 14th International Conference on Medical Image Computing and Computer-Assisted Intervention, MICCAI '11, Toronto, Canada, Sep. 18-22, 2011, 14(Pt.II): 607-614, Sep. 18, 2011.

Graf et al. "Position Prediction in CT Volume Scans", Proceedings of the 28th International Conference on Machine Learning, ICML, Workshop on Learning for Global Challenges, Bellevue, WA, USA, p. 1-4, 2011.

Güld et al. "Quality of DICOM Header Information for Image Categorization", Medical Imaging 2002: PACS and Integrated Medical Information System: Design and Evaluation, Proceedings of the SPIE, 4685: 280-287, May 16, 2002.

Guo et al. "A Deep Learning-Based Method for Relative Location Prediction in CT Scan Images", 31st Conference on Neural Information Processing Systems, NIPS 2017, Long Beach, CA, USA, arXiv Preprint arXiv:1711.07624v1, p. 1-5, Nov. 21, 2017.

OECD "Health at a Glance 2017: OECD Indicators", OECD, p. 1-216, 2017.

\* cited by examiner

SYSTEMS AND METHODS FOR PROCESSING 3D ANATOMICAL VOLUMES BASED ON LOCALIZATION OF 2D SLICES THEREOF

FIELD AND BACKGROUND OF THE INVENTION

The present invention, in some embodiments thereof, relates to 3D anatomical imaging and, more specifically, but not exclusively, to localization of 2D slices of a 3D anatomical volume.

One of the most widely used imaging technology is the Computed Tomography (CT) scan, for example, as described with reference to *OECD. Health at a Glance 2017.* 2017. Unlike 2D imaging modalities, CT scan data is volumetric and is typically composed hundreds or even thousands of 2D images (a.k.a slices). Radiologists may manually review the large number of slices in order to identify a sub-set of slices that include an anatomical region of interest. Automated methods to find the anatomical region of interest include analyzing the large number of slices to extract defined features (e.g., hand crafted features) associated with the anatomical region of interest, and automatically segmenting the anatomical region of interest based on the defined features.

SUMMARY OF THE INVENTION

According to a first aspect, a computer implemented method for localizing target anatomical regions of interest (ROI) of a target individual, comprises: uniformly sub-sampling a plurality of 2D images having sequential index numbers within a 3D anatomical volume, feeding the plurality of sampled 2D images into a classifier for outputting a plurality of values on a normalized anatomical scale, fitting a linear model to the plurality of values and corresponding sequential index numbers, mapping by the linear model, the plurality of 2D images to the normalized anatomical scale, receiving an indication of at least one target anatomical ROI of a target individual, wherein each target anatomical ROI is mapped to the normalized anatomical scale, and providing a sub-set of the plurality of 2D images having values of the normalized anatomical scale corresponding to the received at least one target anatomical ROI.

According to a second aspect, a system for localizing target anatomical regions of interest (ROI) of a target individual, comprises: at least one hardware processor executing a code for: uniformly sub-sampling a plurality of 2D images having sequential index numbers within a 3D anatomical volume, feeding the plurality of sampled 2D images into a classier for outputting a plurality of values on a normalized anatomical scale, fitting a linear model to the plurality of values and corresponding sequential index numbers, mapping by the linear model, the plurality of 2D images to the normalized anatomical scale, receiving an indication of at least one target anatomical ROI of a target individual, wherein each target anatomical ROI is mapped to the normalized anatomical scale, and providing a sub-set of the plurality of 2D images having values of the normalized anatomical scale corresponding to the received at least one target anatomical ROI.

According to a third aspect, a computer program product for localizing target anatomical regions of interest (ROI) of a target individual, comprises: a non-transitory memory storing thereon code for execution by at least one hardware process, the code including instructions for: uniformly sub-sampling a plurality of 2D images having sequential index numbers within a 3D anatomical volume, feeding the plurality of sampled 2D images into a classifier for outputting a plurality of values on a normalized anatomical scale, fitting a linear model to the plurality of values and corresponding sequential index numbers, mapping by the linear model, the plurality of 2D images to the normalized anatomical scale, receiving an indication of at least one target anatomical ROI of a target individual, wherein each target anatomical ROI is mapped to the normalized anatomical scale, and providing a sub-set of the plurality of 2D images having values of the normalized anatomical scale corresponding to the received at least one target anatomical ROI.

In a further implementation of the first, second, and third aspect, further comprising planning a treatment of a patient according to an analysis of the respective sub-set of the plurality of 2D image having values corresponding to the certain target anatomical ROI.

In a further implementation of the first, second, and third aspect, further comprising executing a computer aided diagnosis (CAD) designed for analysis of a certain target anatomical ROI application, on the respective sub-set of the plurality of 2D image having values corresponding to the certain target anatomical ROI.

In a further implementation of the first, second, and third aspect, the normalized anatomical scale comprises a one dimensional coordinate system of a plurality of equally spaced positions along an axial dimension of an arbitrary human body.

In a further implementation of the first, second, and third aspect, the classifier classifies each of the plurality of sampled 2D images into at least one classification category of a plurality of classification categories, wherein the plurality of classification categories correspond to a number of equally spaced values along the normalized anatomical scale.

In a further implementation of the first, second, and third aspect, the classifier computes a mapping confidence score indicative of confidence of the mapping between an inputted 2D image and the computed value, and rejecting the computed value when the mapping confidence score is according to a rejection requirement.

In a further implementation of the first, second, and third aspect, the rejection requirement comprises a plurality of peak probability vectors for a single 2D image.

In a further implementation of the first, second, and third aspect, the 2D image is retained when the mapping confidence score comprises a single and narrow probability vector.

In a further implementation of the first, second, and third aspect, original pixel values of each of the sampled 2D images are inputted into the classifier.

In a further implementation of the first, second, and third aspect, a total number of the plurality of 2D images is about 100-2000, wherein the uniformed sub-sampling is performed by selecting one 2D image for every about 10-50 sequential 2D images, and wherein a number of the sampled 2D images is about 20-50.

In a further implementation of the first, second, and third aspect, the normalized anatomical scale is a continuous range of values ranging from 0 to 99, wherein a normalized position of a tip of a head is set to 0 and a lowest part of feet is set to 99.

In a further implementation of the first, second, and third aspect, the 3D anatomical volume is a CT scan and the plurality of 2D images are axial slices of the CT scan.

In a further implementation of the first, second, and third aspect, the plurality of 2D images are mapped to respective values of the normalized anatomical scale independently of DICOM® metadata associated with the 3D anatomical volume.

In a further implementation of the first, second, and third aspect, the classifier is trained according to a training dataset of 3D anatomical volumes of a plurality of sample patients, where a plurality of 2D images of each 3D anatomical volume are labeled with value on a normalized anatomical scale computed by a process of: labeling each of a superior 2D image and an inferior 2D image with a value corresponding to a respective depicted defined anatomical landmark, labeling 2D images between the superior 2D image and the inferior 2D image with values computed by a linear interpolation of the values of the superior 2D image and inferior 2D image.

In a further implementation of the first, second, and third aspect, the defined anatomical landmark and corresponding value are selected from the group consisting of: tip of head and 0, lateral ventricles and 10.9, hyoid bone and 12.6, superior sternum and 18.9, carina and 21.1, inferior heart and 28.0, $12^{th}$ rib ending and 36.6, superior pelvic bone and 40.0, lesser trochanter and 51.4, patella and 71.4, inferior feet and 100.0.

In a further implementation of the first, second, and third aspect, further comprising computing a fitting score for the fit of the linear model to the plurality of values and corresponding sequential index number of the respective sampled 2D image, wherein a fitting score requirement of the fitting score defines an error in the computation of the values, and rejecting the 3D anatomical volume when the fitting score meets a rejection requirement.

In a further implementation of the first, second, and third aspect, the linear model is selected for fitting to noisy data with strong outliers.

In a further implementation of the first, second, and third aspect, the linear model is based on the Random Sample Consensus (RANSAC) process.

In a further implementation of the first, second, and third aspect, further comprising evaluating the 3D anatomical volume for exclusion from further processing when a set of rules defining unreliable results is met, the set of rules based on a fitting score computed for the linear model and on probability vectors computed by the classifier for the sampled subset of 2D images.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

BRIEF DESCRIPTION OF THE SEVERAL VIEWS OF THE DRAWINGS

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings.

DESCRIPTION OF SPECIFIC EMBODIMENTS OF THE INVENTION

Figure 1:
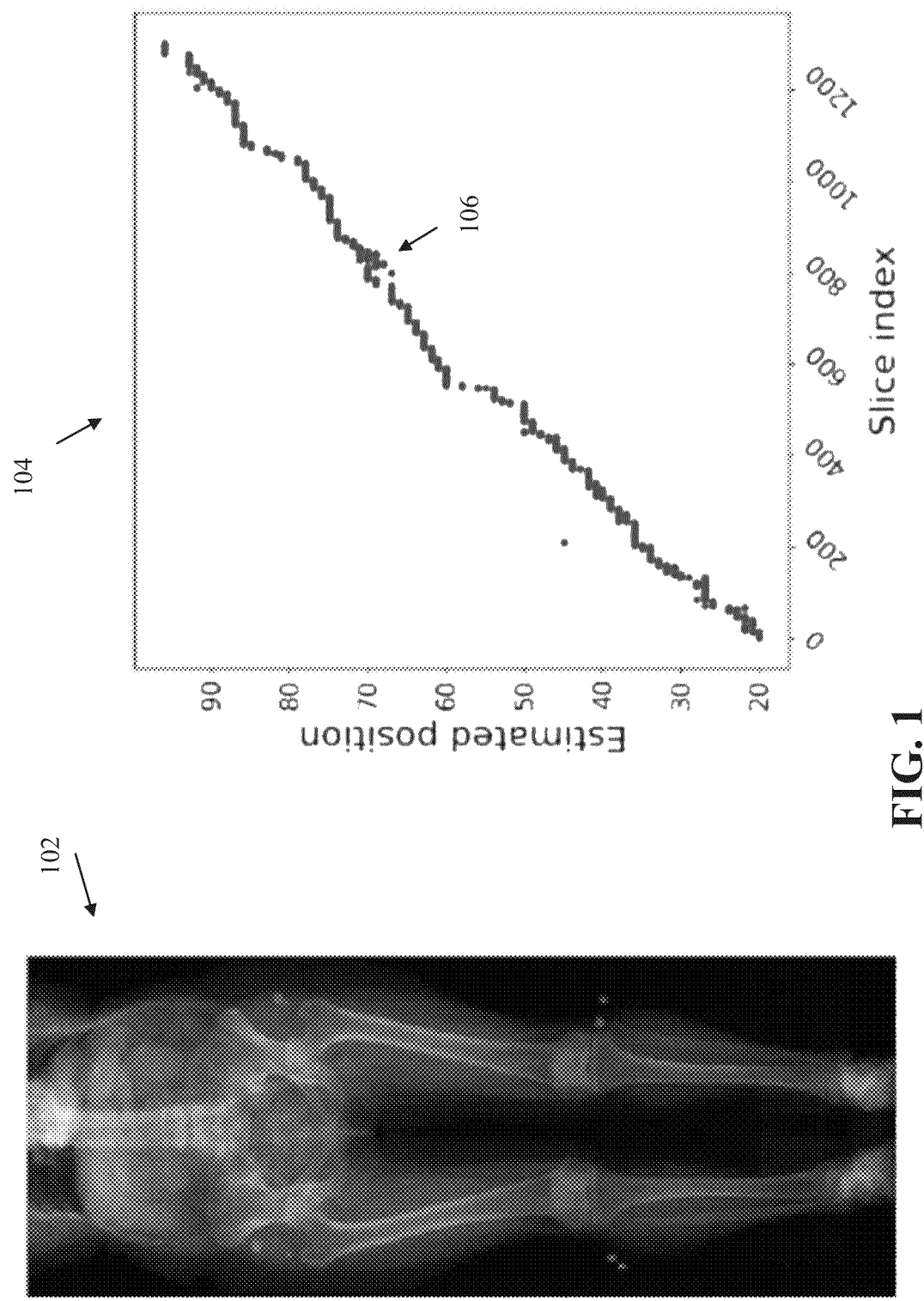
FIG. 1 includes an image summarizing a CT scan, and a graph depicting scan localization results using traditional approaches where every slice was localized independently of other slices, to help understand a technological solution in accordance with some embodiments of the present invention.

The present invention, in some embodiments thereof, relates to 3D anatomical imaging and, more specifically, but not exclusively, to localization of 2D slices of a 3D anatomical volume.

As used herein, the term 3D anatomical volume and 3D anatomical image (or 3D image) may be interchanged. The 3D anatomical volumes and/or images include, for example, output of 3D imaging modality devices, for example, a CT scan by a CT machine, an MRI scan by an MRI machine, a 3D ultrasound scan by a 3D US machine, and a nuclear imaging scan by a nuclear imaging machine.

An aspect of some embodiments of the present invention relates to systems, methods, an apparatus, and/or code instructions for localizing target anatomical regions of interest (ROI) of a target individual. 2D images having sequential index numbers within a 3D anatomical volume are uniformly sub-sampled. For example, a subset of 2D slices of a 3D CT scan (or MRI scan, or nuclear medicine scan, or other imaging modality scans that create 3D anatomical volumes) are uniformly selected, for example, every $5^{th}$ slice, or other values. The sampled 2D images are fed into a classifier for outputting values on a normalized anatomical scale. The normalized anatomical scale is defined, for example, with a lower value (e.g., 0 or other value) set at the lowest point on the body (e.g., bottom of foot) and a highest value (e.g., 99 or other value) set at the highest point on the body (e.g., top of head). The classifier may be trained to output one classification category from multiple candidate classification categories corresponding to the values of the normalized anatomical scale, for example, a value from 0-99 corresponding to the values of the normalized anatomical scale. A linear model is fitted to the values outputted by the classifier for each respective sampled image, and corresponding sequential index numbers of the respective sampled image. The linear model acts as a mapping between index numbers of the 2D images and values on the normalized anatomical scale. The 2D images, including the non-sampled images, are mapped to the normalized anatomical scale by the linear model. An indication of one (or more) target anatomical ROI of a target individual is received, for example, according to a design of a target computed aided diagnosis (CAD) application, and/or manual user input. Candidate anatomical ROI may have predefined mapping to the normalized anatomical scale, for example, certain organs are located at predefined locations on the scale. A sub-set of one or more of the 2D images having values of the normalized anatomical scale corresponding to the received target anatomical ROI are provided.

Optionally, the rest of the 2D images, i.e., other than the sub-set of 2D images having values of the normalized anatomical scale corresponding to the received target anatomical ROI, are not provided, for example, ignored and/or excluded.

Optionally, the set of 2D images are fed into a CAD application designed for analysis of the target anatomical RO. For example, a CAN application that analyzes the liver is fed the subset of 2D slices of a CT scan that depict the liver. The rest of the 2D images are not fed into the CAD application.

Optionally, treatment of a patient is planned according to an analysis of the subset of 2D slices. The treatment may be planned manually and/or automatically by code. For example, treatment on a certain vertebra of the spine is planned, for example, by a surgical planning application, using the subset of 2D slices that depict the certain vertebra.

At least some implementations of the systems, methods, apparatus, and/or code instructions described herein improve medical treatment of a patient, by improving the ability to execute multiple computer aided diagnosis (CAD) applications and/or multiple medical applications (e.g., surgical treatment, surgical simulation) on the same 3D anatomical volume of a patient. Each 3D volume may be analyzed by the different CAD applications to detect indications of different medical conditions. Treatment of the patient may be planned based on the different medical conditions that are detected. As described herein, since each 3D volume is very large, and processing images by CAD applications is computationally intensive, processing each 3D volume by each CAD application for each patient may not be possible using existing resources. At least some implementations of the systems, methods, apparatus, and/or code instructions described herein, which computationally efficiently identify and obtain the 2D images of the 3D volume relevant for each CAD application, significantly reduce the required computational resources, making it possible for the 2D images of each 3D volume to be processed by each CAD application.

At least some implementations of the systems, methods, apparatus, and/or code instructions described herein address the technical problem of executing multiple CAD applications (and/or other applications that processes anatomical portions of images, such as surgical planning applications) on the same 3D anatomical volume (e.g., CT scan). At least some implementations of the systems, methods, apparatus, and/or code instructions described herein improve the technical field of CAD applications, by enabling execution of multiple CAD applications on the same 3D anatomical volume. CAD applications include, for example, tools for the automated measurements, detection and/or classification of anatomical structures, pathology and/or abnormalities which in different modalities and/or imaging techniques. CAD systems are entering the radiology workflow due to their increasing use for assisting radiologists in processing the massive amount of imaging data in 3D anatomical volumes, and/or the vast number of possible visual findings that may be identified in the 3D anatomical volumes. Processing of 3D anatomical volumes for use by CAD applications takes a significantly longer time to process than a single 2D image, since the 3D anatomical volumes include on the order of hundreds or thousands of slices (e.g., megabytes of data). CAD applications are usually based on machine learning processes, which take utilize significant amounts of processing resources (e.g., processor utilization, memory, data storage) to execute and/or take a significant amount of time to execute. The problem is especially challenging when multiple different CAD applications are executed on the same 3D anatomical volume. In such a case, the computational load on the processing computing device (e.g., PACS server, radiologist workstation, client terminal) is significant, taking a very long time to process and/or typing up computational resources that may affect other functions, for example, other radiologists accessing the imaging server may experience delays or difficulty in viewing images. In large imaging facilities that generate large number of 3D volumes on a regular basis, the computational devices may be unable to execute all CAD applications on each 3D volume, or may experience significant time delays. Most CAD applications that process 3D volumes (e.g., CT scans) spend considerable computational resources and/or processing time on first locating the anatomical region of interest (e.g., organ) before analyzing it. For example, a liver lesions detection process needs to first scan the entire 3D imaging volume to locate the liver before actually applying lesion detection on the sub-volume including the liver. Such liver lesion detection process performs faster and/or using fewer computational resources when provided with the sub-volume including the anatomical region of interest instead of the entire 3D anatomical volume (e.g., CT scan) by at least some implementations of the systems, methods, apparatus, and/or code instructions described herein.

At least some implementations of the systems, methods, apparatus, and/or code instructions described herein address the technical problem of identifying an anatomical region of interest in a 3D anatomical volume, in a computationally efficient manner, without using DICOM® metadata (or other corresponding metadata associated with the 3D volume itself). While DICOM® metadata provides information indicating the anatomical region(s) covered in the scan, the metadata is error prone and does not provide the necessary level of granularity (e.g., as described with reference to Daniel Keysers Henning Schubert Berthold B. Wein Joerg Bredno Thomas Martin Lehmann Mark Oliver Gueld, Michael Kohnen. *Quality of dicom header information for image categorization. Proc. SPIE*, 4685:4685-4685-8, 2002) required by organ specific CAD applications. At least some implementations of the systems, methods, apparatus, and/or code instructions described herein process the slices of the 3D anatomical volume directly, independently of DICOM® metadata, without consideration of the metadata.

At least some implementations of the systems, methods, apparatus, and/or code instructions described herein address the technical problem of identifying target anatomical region(s) of interest in a 3D anatomical volume. At least some implementations of the systems, methods, apparatus, and/or code instructions described herein improve computational efficiency of a computing device that identifies the target anatomical region(s) of interest, for example, by reducing required resources (e.g., processor utilization, memory, data storage)) and/or reducing processing time. The improvement is enabled by the computationally efficiency pre-process stage described herein, which maps each slice of the 3D anatomical volume to a unique number which represents the position of the respective slice along an axial dimension of a human body represented by the normalized anatomical scale described herein. Once the entire volume is indexed, different sub-volumes of the 3D volume may be provided to different CAD applications based on their respective anatomical region of interest. The process for mapping each slice of the 3D volume (e.g., CT scan) to a corresponding axial anatomical position is very fast (e.g., about 1 second per CT scan on a PC, regardless of the number of slices, based on an experiment performed by Inventors).

At least some implementations of the systems, methods, apparatus, and/or code instructions described herein address the technical problem of localizing 2D images of a 3D volume corresponding to target ROIs, using a process that supports a wide range of scan regions, protocols and is robust to strong noise levels and artifacts. The process described herein, which is based on the trained classifier outputting classification categories for inputted images (optionally associated with probability values indicative of likelihood of accuracy) and the linear model that is fitted to the outputted values and the index number of the 2D images, is robust to noise, artifacts, regardless of which part of the body is depicted in the 3D volume and/or regardless of which scan protocol was used (e.g., contrast, non-contrast, and the like). The improvement is at least due to the classifier trained on a training dataset including a wide range of scan regions, protocols, noise, and/or artifacts, and the linear model which is fitted using a process robust to outliers (e.g., RANSAC).

At least some implementations of the systems, methods, apparatus, and/or code instructions described herein address the technical problem of localizing every 2D image (i.e., slice) of a 3D anatomical volume (e.g., CT scan) to anatomical locations of the body. In particular, the technical problem is related to performing the localization of each slice in a computationally efficiency manner, with relatively reduced computational resource utilization and/or relatively reduced processing time, in comparison to other methods. As discussed above, localization of the slices of the CT scan may be used to select slices that depict anatomical ROIs. The selected slices may then be, for example, inputted into specialized CAD applications designed to process the anatomical ROIs and/or presented on a display for manual reading by the radiologist (e.g., saving the radiologist the effort of looking for the slices depicting the anatomical ROIs). The technical solution provided by at least some implementations of the systems, methods, apparatus, and/or code instructions described herein is based on a classification problem with a number of different classification classes corresponding to the number of equally spaced intervals of the normalized anatomical scale (e.g., 100). The trained classifier described herein, for example, a convolutional neural network (CNN), receives a 2D slice as input, and outputs an indication of one or more classification classes, optionally associated with a probability value indicative of likelihood of the 2D slice being mapped to the corresponding classification class. The trained classifier, is in contrast to solutions provided by other prior approaches that attempt to localize CT slices based on a regression approach, for example, as described with reference to Franz Graf, Hans-Peter Kriegel, Sebastian Polsterl, Matthias Schubert, and Alexander Cavallaro. *Position prediction in ct volume scans. In Proceedings of the 28$^{th}$ International Conference on Machine Learning (ICML) Workshop on Learning for Global Challenges*, Bellevue, Wash., Wash., 2011, Franz Graf, Hans-Peter Kriegel, Matthias Schubert, Sebastian Plsterl, and Alexander Cavallaro. *2d image registration in ct images using radial image descriptors*. volume 14, pages 607-14, September 2011, and Jiajia Guo, Hongwei Du, Bensheng Qiu, and Xiao Liang. *A deep learning-based method for relative location prediction in CT scan images. CoRR*, abs/1711.07624, 2017. The advantages of the trained classifier over other prior methods is that the probability value computed by the classifier for the classification categories provides a measure of reliability of the localization. Such probability value indicative of likelihood of the respective slices being classified into one or more classification categories, which is computed by at least some implementations of the trained classifier described herein, is not computed by other prior methods such as regression.

At least some implementations of the systems, methods, apparatus, and/or code instructions described herein improve the technical field of image processing, in particular, the process of analyzing 2D slices of 3D anatomical volumes (e.g., slices of a CT scan) for localizing every slice to anatomical locations of the body. The localization, based on the classification of a sampled subset of 2D slices and fitting the linear model to the localized sampled subset of slices, is done with relatively higher accuracy and/or robustness to noise and/or with relatively reduced utilization of processing resources and/or relatively reduced processing time, in comparison to other approaches, for example, approaches that localize each slice independently, one at a time. At least some implementations of the systems, methods, apparatus, and/or code instructions described herein localize 2D images of 3D anatomical volume (e.g., slices of a CT scan), which may include hundreds or even thousands of slices, for example, about 100-2000 slices, or other values. Optionally all 2D slices of the 3D volume are localized.

The improvement in computational efficiency obtained by at least some implementations of the systems, methods, apparatus, and/or code instructions described herein may be at least due to the property of the 2D images being uniformly spaced and ordered along the 3D volume. This property may be exploited to dramatically reduce the amount of computation required to localize an entire scan and to substantially increase the localization accuracy and robustness to different noise sources compared, for example, to straightforward approaches.

Reference is now made to FIG. 1, which includes an image summarizing a CT scan 102, and a graph 104 depicting scan localization results using traditional approaches where every slice was localized independently of other slices, to help understand a technological solution in accordance with some embodiments of the present invention. Processing the approximately 1300 slices of the CT scan 102, independently, one at a time, using traditional approaches, is computationally intensive, takes a considerably long amount of processing time, requires high utilization of processing resources (e.g., processor(s), memory, data storage), is affected by noise, and/or has relatively reduced accuracy. For example, from graph 104 (which plots estimated position relative to slice index), it is apparent that a curve 106 formed by points indicating a mapping between slice index number and estimated position is not straight, indicating effects of noise, outliers, errors, and overall reduced accuracy. In contrast, at least some implementations of the systems, methods, apparatus, and/or code instructions described herein perform mapping of slices to the normalized anatomical scale by a linear model fitted to a sampled subset of the slices that are classified into classification categories by the trained classifier. Instead of localizing every slice, at least some implementations of the systems, methods, apparatus, and/or code instructions described herein estimate the parameters for a linear model based on a small subset of slices and then apply the model to the entire scan. While most localization errors are distributed in a narrow region (e.g., around zero), there are some outliers with very large localization errors. The localization errors are removed or reduced by selection of an appropriate linear model designed to fit to noisy data with strong outliers, as described herein.

Before explaining at least one embodiment of the invention in detail, it is to be understood that the invention is not necessarily limited in its application to the details of construction and the arrangement of the components and/or methods set forth in the following description and/or illustrated in the drawings and/or the Examples. The invention is capable of other embodiments or of being practiced or carried out in various ways.

The present invention may be a system, a method, and/or a computer program product. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Smalltalk, C++ or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/ or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

Figure 2:
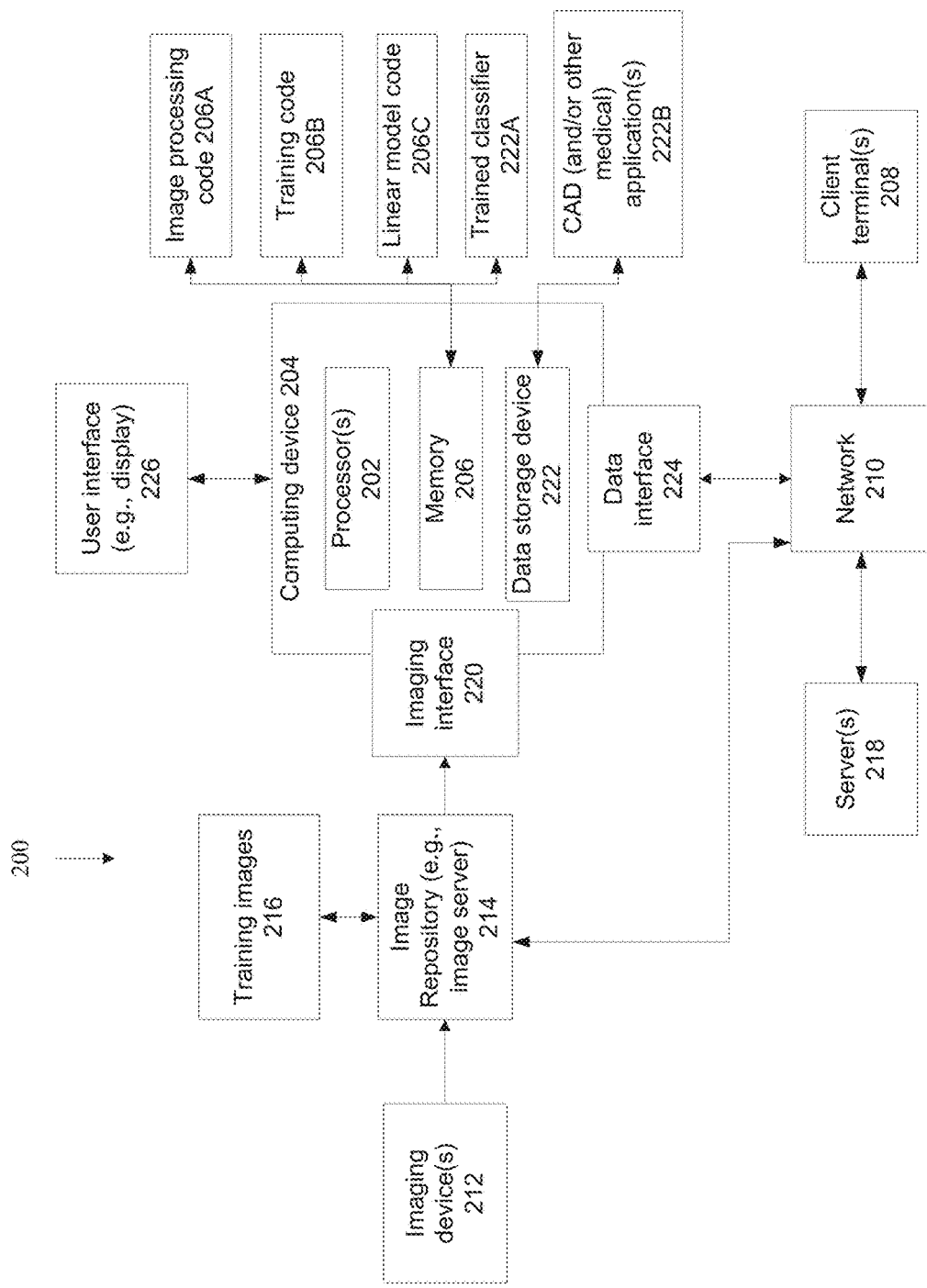
FIG. 2 is a block diagram of a system for localizing target anatomical regions of interest (ROI) of a target individual, based on a classifier that outputs values on a normalized scale in response to input of 2D images of a 3D volume, and a linear model fitted to the outputted values and sequential index numbers of the 2D images, in accordance with some embodiments of the present invention.
Figure 3:
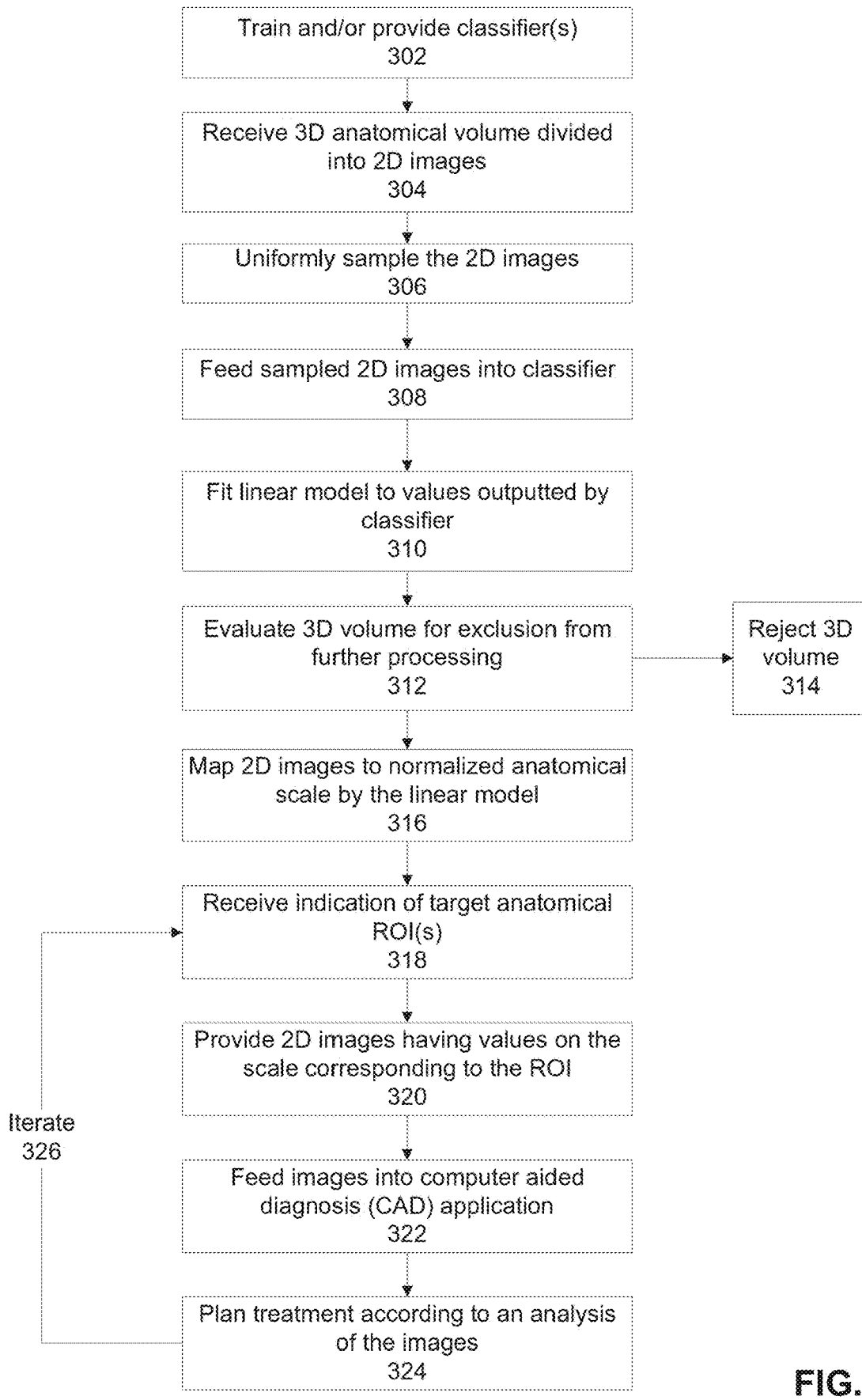
FIG. 3 is a flowchart of a method for localizing target anatomical ROIs of a target individual, based on a classifier that outputs values on a normalized scale in response to input of 2D images of a 3D volume, and a linear model fitted to the outputted values and sequential index numbers of the 2D images, in accordance with some embodiments of the present invention.

Reference is now made to FIG. 2, which is a block diagram of a system 200 for localizing target anatomical regions of interest (ROI) of a target individual, based on a classifier that outputs values on a normalized scale in response to input of 2D images of a 3D volume, and a linear model fitted to the outputted values and sequential index numbers of the 2D images, in accordance with some embodiments of the present invention. Reference is now also made to FIG. 3, which is flowchart of a method for localizing target anatomical ROIs of a target individual, based on a classifier that outputs values on a normalized scale in response to input of 2D images of a 3D volume, and a linear model fitted to the outputted values and sequential index numbers of the 2D images, in accordance with some embodiments of the present invention. System 200 may implement the acts of the method described with reference to FIG. 3, optionally by a hardware processor(s) 202 of a computing device 204 executing code instructions stored in a memory 206.

An exemplary implementation of processing an acquired 3D anatomical volume (e.g., CT scan) is now described to help understand system 200. Imaging device 212 (e.g., CT scanner) acquires a 3D anatomical volume of a target individual, which may be stored in a PACS server 214. Computing device 204 maps (optionally each one of) the 2D slices of the 3D anatomical volume to respective location values of the normalized anatomical scale, by executing trained classifier code 222A and linear model code 206, as described herein. Classifier 222A is generated based on training images 216, as described herein. Different subsets of 2D slices of the 3D anatomical volume, depicting different target anatomical structures of the target individual, are extracted based on a mapping between the respective anatomical structure and location values of the normalized anatomical scale assigned to the 2D slices. For example, one sub-set of 2D slices includes the liver, and another sub-set of 2D slices includes the brain, and yet another sub-set of 2D slices includes the lungs. The sub-sets are provided for analysis, for example, by CAD application 222B.

Computing device 204 may be implemented as, for example, a client terminal, a server, a virtual server, a radiology workstation, a virtual machine, a computing cloud, a mobile device, a desktop computer, a thin client, a Smartphone, a Tablet computer, a laptop computer, a wearable computer, glasses computer, and a watch computer. Computing 204 may include an advanced visualization workstation that sometimes is add-on to a radiology workstation and/or other devices for enabling the user to select 2D slices corresponding to a certain target anatomical structure and/or other computer added detections to the radiologist.

Computing device 204 may include locally stored software that performs one or more of the acts described with reference to FIG. 1 and/or FIG. 3, and/or may act as one or more servers (e.g., network server, web server, a computing cloud, virtual server) that provides services (e.g., one or more of the acts described with reference to FIG. 1 and/or FIG. 3) to one or more client terminals 208 (e.g., client terminal used by a user for viewing anatomical images, client terminal running CAD application(s) for automated analysis of the volumes, remotely located radiology workstations, remote picture archiving and communication system (PACS) server, remote electronic medical record (EMR) server) over a network 210, for example, providing software as a service (SaaS) to the client terminal(s) 208, providing an application for local download to the client terminal(s) 208, as an add-on to a web browser and/or a medical imaging viewer application, and/or providing functions using a remote access session to the client terminals 208, such as through a web browser, application programming interface (API), and/or software development kit (SDK), for example, for integrating CAD applications with the computing device 204 to enable the CAD application to request a sub-set of 2D slices that include the target anatomical structure(s) that the CAD application is designed to detect.

Client terminal(s) 208 may be implemented as, for example, a radiology workstation, a desktop computer (e.g., running a PACS viewer application and/or CAD application), a mobile device (e.g., laptop, smartphone, glasses, wearable device), and nurse station server.

Is it noted that the training of the classifier, and the application of the trained classifier to anatomical images to compute a classification category indicative of location on the normalized anatomical scale, may be implemented by the same computing device 204, and/or by different computing devices 204, for example, one computing device 204 trains the classifier, and transmits the trained classifier to a server device 204.

Computing device 204 receives 3D anatomical volumes (in which case computing device 204 may compute the 2D slices), and/or receives the 2D slices of the 3D anatomical volume, captured by an anatomical imaging device(s) 212, for example, a computer tomography (CT) machine. 3D anatomical volumes (and/or 2D slices thereof) captured by imaging machine 212 may be stored in an image repository 214, for example, a storage server (e.g., PACS server), a computing cloud, virtual memory, and a hard disk. Training images 216 are created based on the 3D anatomical volumes, as described herein.

Training images 216 are used to train the classifier, as described herein. It is noted that training images 216 may be stored by a server 218, accessibly by computing device 204 over network 210, for example, a publicly available dataset of images (that are labeled as described herein), and/or a customized training dataset created for training the classifier, as described herein.

3D anatomical volumes captured by imaging machine(s) 212 depict anatomical features and/or anatomical structures within the body of the target patient. Exemplary 3D anatomical volumes include: fully body scan, head scan, chest scan, abdominal scan, chest and abdomen scan, scan with contrast, scan without contrast, and combinations of the aforementioned.

Computing device 204 may receive the 3D anatomical volumes for mapping to location values of the normalized anatomical scale, and/or receive training images 216, from imaging device 212 and/or image repository 214 using one or more imaging interfaces 220, for example, a wire connection (e.g., physical port), a wireless connection (e.g., antenna), a local bus, a port for connection of a data storage device, a network interface card, other physical interface implementations, and/or virtual interfaces (e.g., software interface, virtual private network (VPN) connection, application programming interface (API), software development kit (SDK)).

Hardware processor(s) 202 may be implemented, for example, as a central processing unit(s) (CPU), a graphics processing unit(s) (GPU), field programmable gate array(s) (FPGA), digital signal processor(s) (DSP), and application specific integrated circuit(s) (ASIC). Processor(s) 202 may include one or more processors (homogenous or heterogeneous), which may be arranged for parallel processing, as clusters and/or as one or more multi core processing units.

Memory 206 (also referred to herein as a program store, and/or data storage device) stores code instruction for execution by hardware processor(s) 202, for example, a random access memory (RAM), read-only memory (ROM), and/or a storage device, for example, non-volatile memory, magnetic media, semiconductor memory devices, hard drive, removable storage, and optical media (e.g., DVD, CD-ROM). For example, memory 206 may store image processing code 206A that implement one or more acts and/or features of the method described with reference to FIG. 1, and/or training code 206B that execute one or more acts of the method described with reference to FIG. 3, and/or code instructions of trained classifier 222A and/or code instructions of linear model 206C, and/or CAD application code 222B.

Alternatively or additionally, client terminal(s) 208 and/or server 218 may locally store and/or execute CAD application code 222B and/or training code 206B.

Computing device 204 may include a data storage device 222 for storing data, for example, a trained classifier 222A, linear model code 206C, training images 216, and/or CAD application(s) 222B. Data storage device 222 may be implemented as, for example, a memory, a local hard-drive, a removable storage device, an optical disk, a storage device, and/or as a remote server and/or computing cloud (e.g., accessed over network 210). It is noted that trained classifier 222A, linear model code 206C, training images 216, and/or CAD application(s) 222B may be stored in data storage device 222, with executing portions loaded into memory 206 for execution by processor(s) 202.

Computing device 204 may include data interface 224, optionally a network interface, for connecting to network 210, for example, one or more of, a network interface card, a wireless interface to connect to a wireless network, a physical interface for connecting to a cable for network connectivity, a virtual interface implemented in software, network communication software providing higher layers of network connectivity, and/or other implementations. Computing device 204 may access one or more remote servers 218 using network 210, for example, to download updated training images 216 and/or to download an updated version of image processing code, training code, CAD application(s), and/or the trained classifier.

It is noted that imaging interface 220 and data interface 224 may be implemented as a single interface (e.g., network interface, single software interface), and/or as two independent interfaces such as software interfaces (e.g., as APIs, network ports) and/or hardware interfaces (e.g., two network interfaces), and/or combination (e.g., single network interface, and two software interfaces, two virtual interfaces on a common physical interface, virtual networks on a common network port). The term/component imaging interface 220 may sometimes be interchanged with the term data interface 224.

Computing device 204 may communicate using network 210 (or another communication channel, such as through a direct link (e.g., cable, wireless) and/or indirect link (e.g., via an intermediary computing device such as a server, and/or via a storage device) with one or more of:

Client terminal(s) 208, for example, when computing device 204 acts as a server that maps the 2D slices to location values on the normalized anatomical scale. Client terminal 208 may request certain 2D slices from computing device 204 having location values corresponding to target anatomical structures. The obtained 2D slices may be, for example, presented within a viewing application for viewing (e.g., by a radiologist) and/or automatically processed (e.g., by CAD application 222B installed on client terminal 208).

Server 218. In one implementation, server 218 is implemented as image server 214, for example, a PACS server. Server 218 may store new 3D anatomical images as they are captured, and/or may store the training dataset. In another implementation, server 218 is in communication with image server 214 and computing device 204. Server 218 may coordinate between image server 214 and computing device 204, for example, transmitting newly received 3D anatomical volumes from server 218 to computing device 204 for mapping the 2D slices to location values of the normalized anatomical scale. In yet another implementation, server 218 may perform one or more features described with reference to client terminal(s) 208, for example, requesting certain 2D slices from computing device 204 having location values corresponding to target anatomical structures, for presentation on a display and/or for inputting into CAD application(s) 222B (which may be locally installed on server) 218.

Anatomical image repository 214 that stores 3D anatomical volumes (and/or 2D slices thereof) and/or imaging device 212 that outputs the 3D anatomical volumes (and/or 2D slices thereof).

Computing device 204 and/or client terminal(s) 208 and/or server(s) 218 include or are in communication with a user interface 226 that includes a mechanism designed for a user to enter data (e.g., select target anatomical structure(s) for obtaining corresponding 2D slices depicting the target anatomical structure(s), select CAD applications for execution) and/or view the obtained 2D images and/or view the results of the executed CAD applications. Exemplary user interfaces 226 include, for example, one or more of, a touchscreen, a display, a keyboard, a mouse, and voice activated software using speakers and microphone.

Referring now back to FIG. 3, at 302, one or more classifiers are trained and/or provided. The classifier may be implemented, for example, as a convolutional neural network (CNN), and/or regressor.

It is noted that the regressor outputs a continuous number in the range defined by the normalized anatomical scale.

Multiple classifiers may be trained and/or provided, for example, based on imaging modality and/or protocol of acquisition of a 3D anatomical volume, for example, for CT scans, for MRI, scans, for nuclear medicine scans, for PET scans, for contrast scans, for non-contrast scans, and/or combinations of the aforementioned.

The classifier is trained to classify inputted 2D images (i.e., obtained by uniformly sub-sampling a 3D anatomical volume, as described herein) into classification categories corresponding to a number of equally spaced values along a normalized anatomical scale. For example, the classifier outputs where on the normalized anatomical scale the 2D image best fits, for example, within 0-99, optionally discrete numerical values. The classifier may output a probability value for each one of the values of the normalized anatomical scale indicative of the probability that the respective 2D image corresponds that the respective value on the scale, for example, as a vector having a size corresponding to the number of values on the scale (e.g., 100), with a probability value assigned to each value of the vector. It is noted that a threshold may be applied to the probability values to obtain the classification result, for example, the value of the scale is selected when the probability value is above 90%, or other values.

Optionally, the normalized anatomical scale is a one dimensional coordinate system of equally spaced positions along an axial dimension of an arbitrary human body. The one dimensional coordinate system may be described, for example, with reference to Tobias Emrich, Franz Graf, Hans-Peter Kriegel, Matthias Schubert, Marisa Thoma, and Alexander Cavallaro. Ct slice localization via instance-based regression. In *Medical Imaging: Image Processing*, 2010 and/or Johannes Feulner, S. Kevin Zhou, Sascha Seifert, Alexander Cavallaro, Joachim Hornegger, and Dorin Comaniciu. *Estimating the body portion of ct volumes by matching histograms of visual words. Proceedings of SPIE—The International Society for Optical Engineering*, February 2009. The anatomical scale may be invariant to the height and/or scan resolution of the respective patient. The normalized anatomical scale may enable reducing the problem of localizing 2D images of the 3D volumes (e.g., 2D slices of the CT scan) to the problem of mapping the 2D images to a scalar in the range defined by the normalized anatomical scale (e.g., [0.,99]).

The normalized anatomical scale is a continuous range of values ranging, for example, from 0 to 99, or 1 to 100, or 0 to 10, or 1 to 1000, or other ranges. A normalized position of a tip of a head is set to the lowest value of the scale (e.g., 0 or other value) and a lowest part of feet is set to the highest value of the scale (e.g., 99 or other value). In another implementation, a normalized position of a tip of a head is set to the highest value of the scale and a lowest part of feet is set to the lowest value of the scale.

The same scale may be used for men, women, children, regardless of size and/or weight. Alternatively, different scales may be used for different categories of people, for example, one scale for children, and another for adults, since the proportion of body parts in children is different than in adults. Different classifiers may be trained on different scales. The type of scale may be selected, for example, based on code that automatically analyzes the image, based on metadata, based on the patient health record, and/or based on manual user input.

The classifier is trained according to a training dataset of labeled 3D anatomical volumes of sample patients, for example, full body CT scans. The 2D images of the 3D anatomical volumes (e.g., slices of a CT scan) are labeled and/or tagged with a value of the normalized anatomical scale. The values may be computed by the following exemplary process: A superior 2D image and an inferior 2D image are labeled with a value corresponding to a respective depicted defined anatomical landmark. The superior and inferior 2D images represent the upper and lower 2D images where the anatomical landmark first appears. 2D images before the superior 2D image and 2D images after the inferior image do not depict the anatomical landmark. The anatomical landmark spans several consecutive 2D images. The anatomical landmarks may be distinct, having values on the scale based on relative position in a human body, optionally a health and/or normal human body, for example, excluding anatomical abnormalities and/or bodies having extreme values on a normal distribution (e.g., very large, very small). Exemplary anatomical landmark and corresponding values are selected from the group consisting of: tip of head and 0, lateral ventricles and 10.9, hyoid bone and 12.6, superior sternum and 18.9, carina and 21.1, inferior heart and 28.0, $12^{th}$ rib ending and 36.6, superior pelvic bone and 40.0, lesser trochanter and 51.4, patella and 71.4, inferior feet and 100.0. The labeling may be performed, for example, manually by a user using a designed graphical user interface, and/or automatically by code designed to automatically segment the anatomical landmark. 2D images between the superior 2D image and the inferior 2D image are labeled with values computed by a linear interpolation of the values of the superior 2D image and inferior 2D image. The process of labeling the extreme anatomical landmarks is computationally efficient, since 2D images between the images depicting the extreme anatomical landmarks are automatically labeled based on the values of the extreme 2D images.

When the 3D volume depicts a full human body (e.g., full body CT scans), the extreme slices may depict the extreme anatomical landmarks corresponding to the lower and highest values on the scale (e.g., tip of head at 0.0 and inferior feet at 100.0).

It is noted that the process automatically and accurately labels other 3D volumes that depict partial body parts, based on identification of 2D images that depict the most extreme (e.g., highest and lowest) anatomical landmarks in the body part, for example, head scan, abdomen scan, chest scan, and abdominal-chest scan.

The training dataset used to create the classifier may include 3D volumes from a variety of: scan protocols, depicting deformations, and/or depicting artifacts including the presence of objects (e.g., pacemaker, screws, metallic hip and/or knee joint, amalgam fillings, and the like).

Different datasets of different imaging volumes from different imaging modalities may be created to train classifiers for the 3D volumes of different imaging modalities.

It is noted that partial body scans may be used, with the highest and lowest parts of the body depicted in the CT scan being assigned the corresponding value of the anatomical scale.

Figure 4:
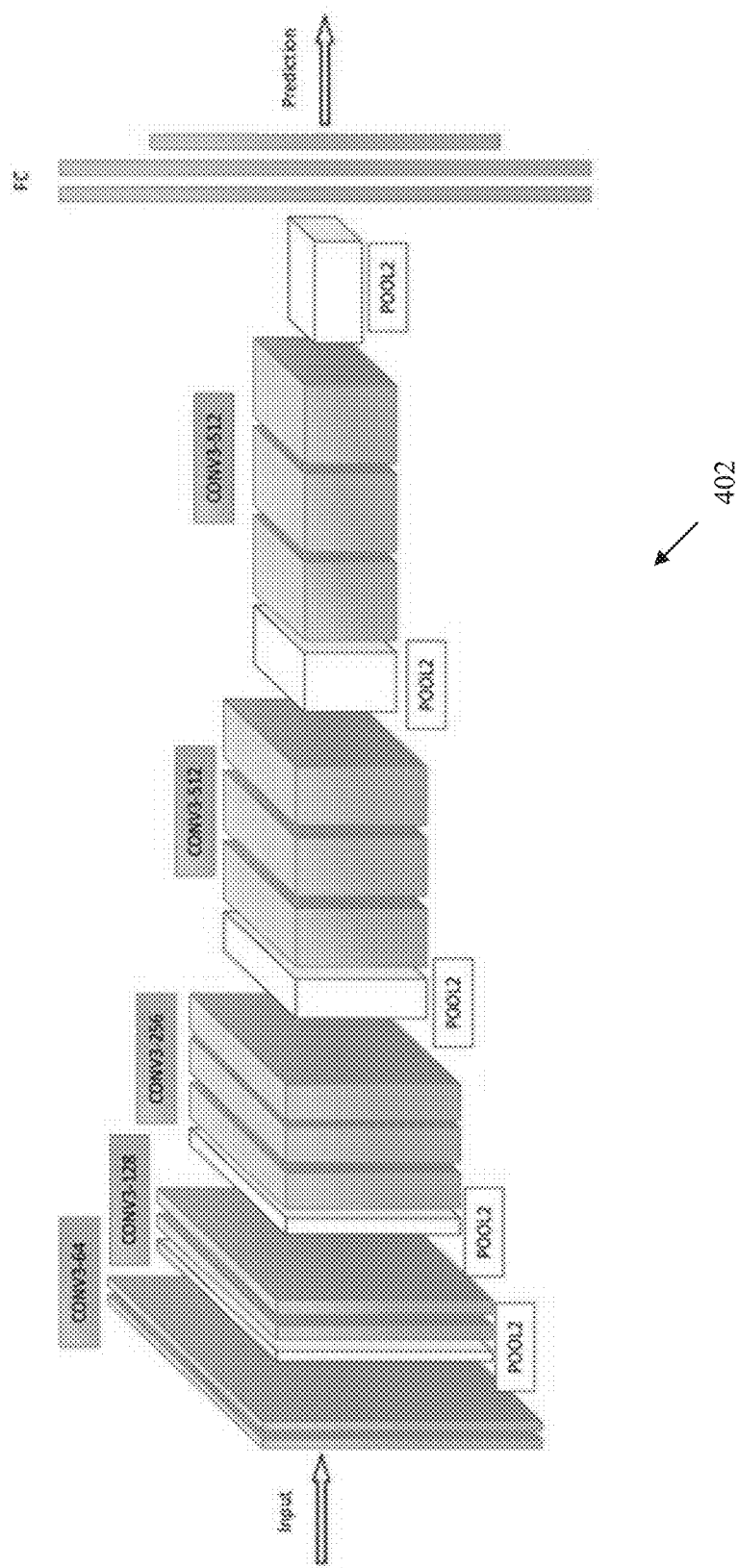
FIG. 4 is a schematic of an exemplary architecture of a CNN 402 implementation of the classifier that maps inputted 2D images to values of a normalized anatomical scale, in accordance with some embodiments of the present invention.

Reference is now made to FIG. 4, which is a schematic of an exemplary architecture of a CNN 402 implementation of the classifier that maps inputted 2D images to values of a normalized anatomical scale, in accordance with some embodiments of the present invention. As discussed herein, the CNN implementation is one example, and other implementations and/or architectures are possible, for example, variations of the CNN architecture 402, other neural network architectures, and/or other classifier architectures, for example, a regressor.

Optionally, CNN 402 includes with a single channel 256×256 input image and a softmax-normalized output vector of length 100. Optional preprocessing includes the resizing of the original 512×512 CT slices to 256×256 slices, for example, using bi-linear interpolation. The original pixel values which indicate Hounsfield units are not (necessarily) rescaled.

At 304, the 3D anatomical volume is received. The 3D anatomical volume may be obtained, for example, from the medical imaging storage server (e.g., PACS), from the electronic health record (EHR) of the patient, from the imaging device, and/or from a storage device (e.g., CD-ROM, cloud storage, hard disk, disk on key). 3D anatomical volumes may be automatically received, for example, upon capture by the imaging device, and/or in batch form (e.g., nightly processing of images captured during the day).

Each 3D anatomical volume is divided into sequential 2D images, optionally sequential slices. The slices may be uniformly spaced. The slices may overlap, and/or may be non-overlapping. The slices may be axial slices. Slices at other planes may be used, in which case the normalized anatomical scale is designed perpendicular to the slicing plane, and the classifier is trained accordingly on a training dataset of labeled 2D slices at the selected plane.

The 2D images are assigned sequential index numbers within the 3D anatomical volume. For example, the first 2D image is assigned the value of 0 or 1, with each subsequent 2D image having a number greater by 1. For example, a total number of the 2D images is about 100-2000 or about 500-3000, or about 1000-2000, or other values.

It is noted that the index number may be assigned independently of metadata stored in association with the 3D volume, for example, DICOM® metadata. Such metadata may include, for example, slice numbers, which may be incorrect.

The 3D anatomical volume may be outputted, for example, by a CT scanner, an MRI machine, a PET scanner, a nuclear medicine machine, a 3D ultrasound scanner, and combinations of the aforementioned.

At 306, the 2D images are uniformly sampled. The uniform sub-sampling is performed by selecting one 2D image for every, for example, about 10-50 sequential 2D images. The number of the sampled 2D images is, for example, about 20-50.

At 308, the sampled 2D images are fed into the classifier. Optionally, the original pixel values of each of the sampled 2D images are inputted into the classifier. The 2D images are not necessarily pre-processed for adjustment of pixel values prior to being fed into the classifier.

The classifier outputs a value on the normalized anatomical scale for each inputted 2D image.

Optionally, the classifier computes a mapping confidence score indicative of confidence of the mapping between an inputted 2D image and the computed value. The mapping confidence score may be, for example, a probability value. Mapping confidence scores may be computed for each candidate value that the classifier may output values for, for example, as a vector. For example, the classifier outputs a vector of size 100 corresponding to the 100 divisions of the anatomical scale, with a mapping confidence score computed for each of the 100 values indicative the probability that the 2D image maps to each of the 100 locations on the anatomical scale. Conceptually, since the 2D image actually only corresponds to a single location, the probability values may be analyzed to select the value on the scale mapped to the 2D image, for example, as the peak mapping confidence score, and/or mapping confidence score above a threshold value indicating high likelihood (e.g., over 90%, or over 80%, or over 95%, or other values).

Optionally, the computed value is rejected when the mapping confidence score is according to a rejection requirement. The rejection requirement may be defined as multiple peak probability values (e.g., vectors) for a single 2D image, where each peak may be defined according to a peak definition, for example, above a threshold probability value, and/or a probability value greater by a defined amount with respect to other probability values. The presence of multiple peaks indicates that the single image maps to multiple different locations on the anatomical scale, which is incorrect, since the single image maps to only one location. Alternatively or additionally, the rejection requirement may be defined as a mapping confidence value below a threshold denoting low likelihood of correct mapping, for example, below about 90%, or 80%, or 70%, or other values. Additional details and examples are described below in the "Examples" section with reference to FIG. 6.

Optionally, the 2D image is retained when the mapping confidence score comprises a single and narrow probability vector, and/or is above the threshold indicative of high likelihood.

At 310, a linear model is fitted to the values (outputted by the classifier) and corresponding sequential index numbers.

The linear model may be selected when the 2D images (e.g., slices) of the 3D volume are uniformly spaced, and when the anatomical scale has uniformly spaced values, based on the assumption that the mapping between the anatomical scale and the index numbers of the 2D images is linear.

Optionally, the linear model is selected for fitting to noisy data with strong outliers. The strong outlier may be rejected by the linear model, for example, the strong outliers represent errors in classification of the 2D images, and therefore should be ignored in the fitting of the linear model. The linear model may be based, for example, on the Random Sample Consensus (RANSAC) process, which is very robust to outliers, for example as described with reference to Martin A. Fischler and Robert C. Bolles. *Random sample consensus: A paradigm for model fitting with applications to image analysis and automated cartography. Commun. ACM,* 24(6):381-395, June 1981.

At 312, the 3D volume may be evaluated for exclusion from further processing, for example, when a set of rules defining unreliable results is met. The set of rules may be based on a fitting score computed for the linear model and on probability values (e.g., stored in a vector) outputted by the classifier for the sampled subset of 2D images.

The fitting score may be computed for the fit of the linear model to the values and corresponding sequential index number of the respective sampled 2D image. A fitting score requirement of the fitting score defines an error in the computation of the values. The fitting score requirement may be, for example, a threshold value, where fitting scores below the threshold represent an error in computation of the values.

The linearity assumption, that the 2D images of the 3D anatomical volume are uniformly spaced and ordered, may act as a fail-safe mechanism for excluding the 3D volume according to the fitting score.

The fitting score may be, for example, as the score indicative of the fit of the RANSAC process to the values and corresponding sequential index number of the respective sampled 2D image.

At 314, the 3D anatomical volume may be rejected, for example, when a set of rules is met. The set of rules may discriminate reliable results of mapping 2D images of the 3D volume to locations on the anatomical scale from unreliable results. The set of rules may be based on the fitting score (e.g. computed for the process used to fit the linear model) and/or based on the probability values (e.g., of the vector) outputted by the classifier for the selected sampled 2D images. The probability value is indicative of likelihood of accurate mapping between the respective 2D image and values (e.g., each value) on the normalized anatomical scale.

Optionally, the set of rules and/or fitting score is evaluated according to a rejection requirement.

The 3D anatomical volume may be rejected when the localization process of mapping 2D images to the anatomical scale is determined to be incorrect based on the fitting score, optionally according to the set of rules.

An error indication may be generated that the process has terminated unsuccessfully, for example, a message appears on a display of an administrator, an email is sent to an inbox of an administrator, and/or a tag is added to a medical and/or imaging record.

The vector of a size corresponding to the anatomical scale with a probability computed for each value of the scale may be computed for each sampled 2D image, as described herein, where the probability value is indicative of likelihood of the respective 2D image mapping to the respective anatomical location on the scale. The vector may be analyzed to determine whether to reject the 3D anatomical volume optionally according to the set of rules. For example, when each vector of the sampled 2D images stored one high probability value, the 3D volume may be determined to be reliable. The high probability value (e.g., peak value) may be defined, for example, as a single value of the scale above a threshold (e.g., above 80% or 90% or other values), and/or a maximal value that is higher than other neighboring values by a requirement (e.g., higher by 50%, or 60%, or double, or triple, or other values). Vectors of 2D images having multiple peaks (e.g., two values above the threshold, for example, two locations on the scale having probability values of >85%), or spread out high probability values (e.g., spread out peaks, for example, three consecutive values on the scale all having values close to one another below a requirement, for example, 68%, 85%, and 73%) may denote erroneous 3D volumes that are to be rejected, optionally according to the set of rules.

Alternatively or additionally, certain 2D images identified as outliers are excluded and/or ignored, with processing proceeding for the remaining 2D images of the 3D volume, optionally according to the set of rules.

Alternatively, when the set of rules and/or the fitting score do not meet the rejection requirement, act 316 is implemented. Act 316 may be implemented when certain 2D images are excluded, by processing the remaining 2D images.

At 316, the 2D images are mapped by the linear model to the normalized anatomical scale. The 2D images that are mapped by the linear model may be the non-selected 2D images which were not uniformly sampled and not fed into the classifier. Alternatively or additionally, the 2D images that are mapped by the linear model may include the sampled 2D image (e.g., all of the 2D images of the 3D volume). In such a case, the linear model may be used to re-compute values for the sampled 2D images which were fed into the classifier. The re-computing of the values may smooth out errors of the classifier, by aligning all of the 2D images along the scale according to the linear model.

It is noted that the 2D images may be mapped to respective values of the normalized anatomical scale independently of metadata associated with the 3D anatomical volume, for example, independently of DICOM® metadata. Such metadata may be erroneous. For example, the metadata may store incorrect indications of slice number and/or be incorrect in the anatomical features depicted in the respective 2D image.

At 318, receiving an indication of one or more target anatomical ROI of a target individual. The target individual is the same patient depicted in the 3D anatomical volume that is being processed.

The indication of the target anatomical ROI may be obtained, for example, by executing code associated with a target application designed to analyze images depicting the target anatomical ROI (e.g., CAD application), by a user manually entering a selected ROI, selected from a set of predefined ROIs, and/or the target ROIs may be predefined and stored in a data storage device.

The target anatomical ROIs may include anatomical landmarks and/or features depicted in images, for example, heart ventricle, liver, certain lymph nodes, brain, lung, certain spinal vertebra, and femur.

Each target anatomical ROI may be pre-mapped to the normalized anatomical scale, for example, stored as key-value pairs, in a dataset, and/or other methods.

Each target anatomical ROI may be mapped to one or multiple values of the normalized anatomical scale, for example, a range.

At 320, the 2D images having values of the normalized anatomical scale corresponding to the received target anatomical ROI are provided.

The selected set of 2D images may be provided, for example, presented on a display of a client terminal for visual inspection (e.g., presented by a PACS viewer on a radiology workstation), stored in a storage device (e.g., CD-ROM or disk on key provided to the patient), stored in a server, and/or provided to another executing process for further process.

At 322, the provided sub-set of 2D images having values of the scale corresponding to the target anatomical ROIs may be fed into a computer aided diagnosis (CAD) process designed for analysis of a certain target anatomical ROI application. For example, the sub-set of 2D images corresponding to the liver are fed into a CAD process that segments the liver and analyzes the liver to detect an indication of fatty liver and/or colon cancer metastases.

At 324, treatment of a patient may be planned according to an analysis of the respective sub-set of the 2D image having values corresponding to the certain target anatomical RO. The treatment may be planned, for example, based on a visual assessment of the sub-set of images, based on an automated assessment by code (e.g., by the CAD application), and/or by treatment planning application designed for treatment of the target ROI (e.g., manually and/or automatically) such as surgical simulation and/or surgical planning applications.

At 326 one or more features described with reference to acts 118-124 may be iterated, for example, in parallel, and/or sequentially. For example, different target ROIs may be received (e.g., lung, liver, bladder) and the corresponding sets of 2D images are provided to different CAD applications each designed to process images depicting the respective ROIs. For example, one CAD application designed to detect lung cancer, another CAD application designed to detect fatty liver, and a third CAD application designed to detect bladder cancer.

Various embodiments and aspects of the present invention as delineated hereinabove and as claimed in the claims section below find calculated support in the following examples.

EXAMPLES

Reference is now made to the following examples of training the classifier and localizing CT slices by the trained classifier and the linear model, which together with the above descriptions illustrate some implementations of the systems, methods, apparatus, and/or code instructions described herein in a non limiting fashion.

Inventors used the 1 dimensional normalized anatomical scale divided into 100 parts, where the tip of the head is set to 0 and the lowest part of the feet is set to 99, as described herein.

The classifier used for the experimental evaluation is the CNN as described with reference to FIG. 4. The CNN had a single channel 256×256 input image, and a softmax-normalized output vector of length 100 (corresponding to the 100 equally spaced divisions of the normalized anatomical scale), as described herein. Preprocessing included only the resizing of the original 512×512 CT slices to 256×256 slices using bi-linear interpolation. The original pixel values which indicate Hounsfield units were not rescaled.

The training dataset was created by labeling CT volumes of sample subjects as follows: given a CT scan, a trained annotator located the slices showing the superior (uppermost) and inferior (lowermost) visible anatomical landmarks out of the 11 landmarks as described herein. Those two slices were assigned with the landmarks' corresponding values. All the slices between those two extreme slices were assigned with the linear interpolation of the extreme slices' normalized positions.

The training set included 248 scans of 124 adult males and 124 adult females. The scans were chosen to include a variety of scan protocols, deformations and artifacts inducing objects (e.g., pacemakers, screws, metallic hip and knee joints, amalgam fillings, and the like). The CT scans produced a collection of almost 60,000 slices which were sub-sampled so that only the first out of every three consecutive slices was included in the training set resulting in 19287 slices.

The validation set was curated by the same criteria and included 26 scans of 13 adult males and 13 adult females. After sub-sampling, it included 2355 slices.

Training was performed over 50 epochs using Adam optimizer and categorical cross-entropy loss. The learning rate was $10^{-4}$ for the first 30 epochs, $10^{-5}$ for the next 10 epochs and $10^{-6}$ for the last 10 epochs. Data augmentation included zoom, rotation, shear, horizontal and vertical flips.

Figure 5:
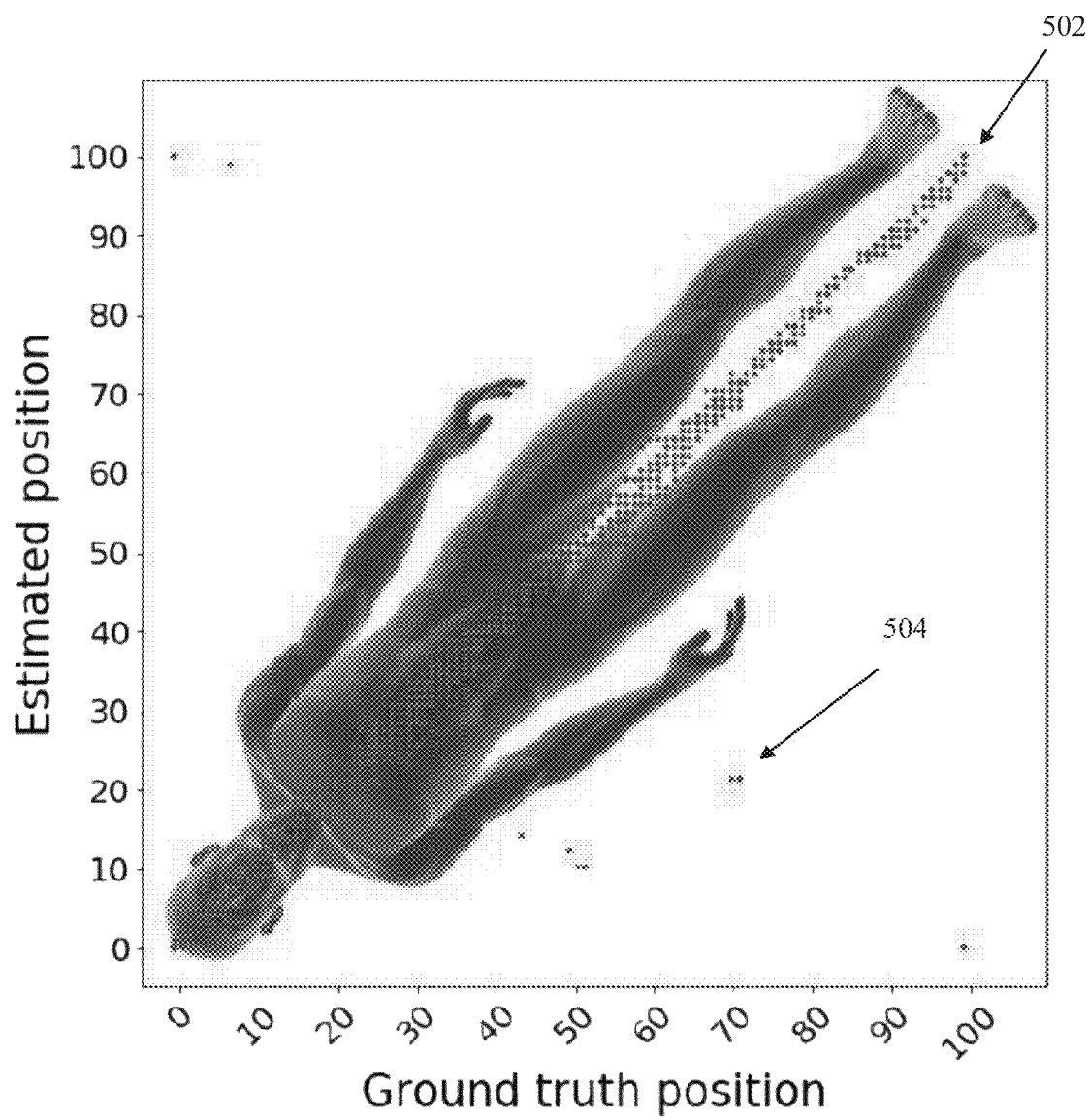
FIG. 5 is a graph depicting predicted versus ground truth labels for the entire validation set of the experimental evaluation, computed by the trained classifier, in accordance with some embodiments of the present invention.

Reference is now made to FIG. 5, which is a graph 502 (i.e., of points) depicting predicted versus ground truth labels for the entire validation set of the experimental evaluation, computed by the trained classifier, in accordance with some embodiments of the present invention. The classification analysis shows a median error of 1 unit and an average of 1.4 units. As demonstrated, while most localization errors are distributed in a narrow region around zero, there are some outliers with very large localization errors, for example, the dots pointed to by arrow 504.

Figure 6:
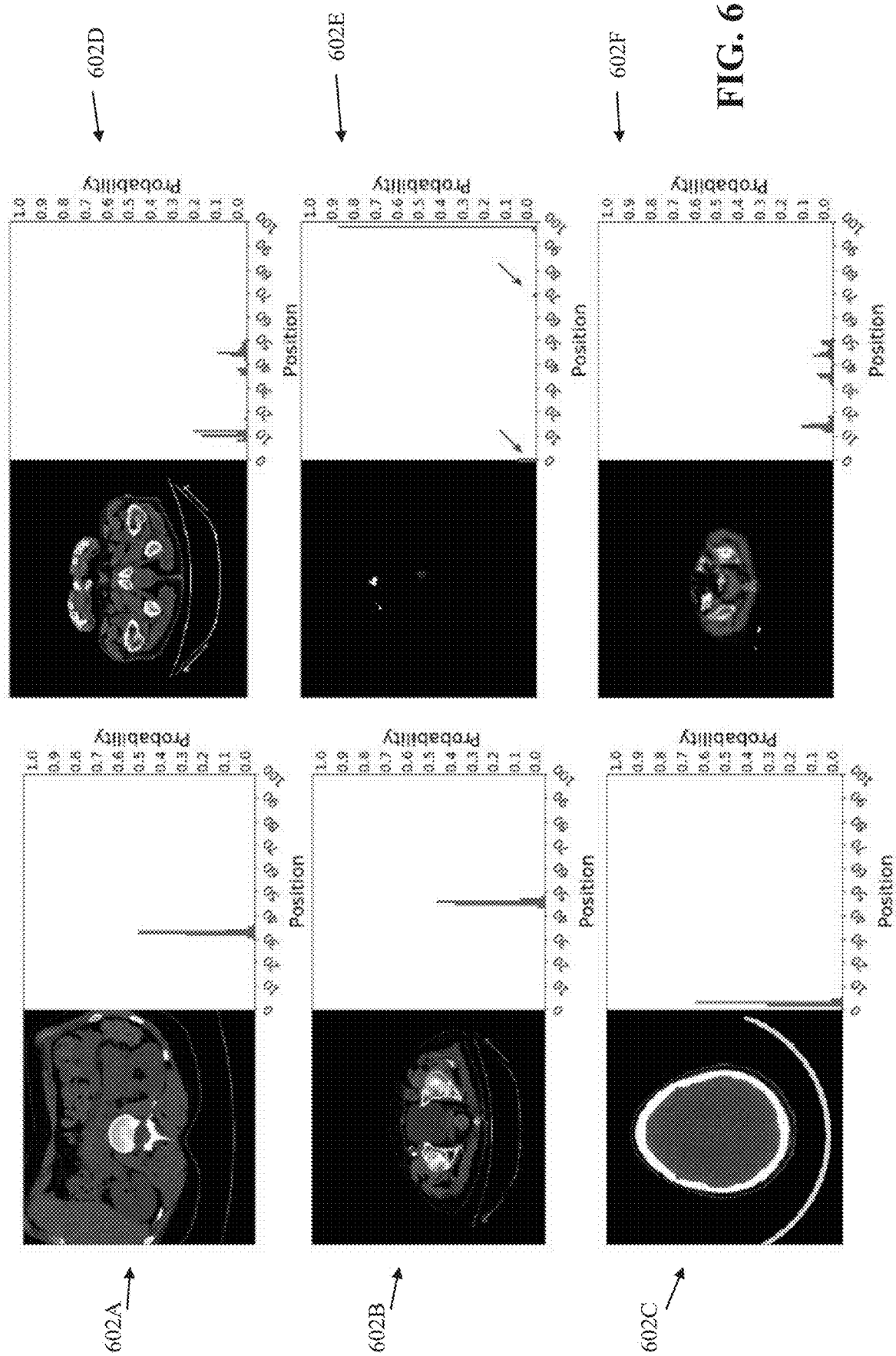
FIG. 6 includes graphs depicting example slices and corresponding probabilities for classified classes computed by the trained classifier for the experimental evaluation, in accordance with some embodiments of the present invention.

Reference is now made to FIG. 6, which include graphs depicting example slices and corresponding probabilities for classified classes computed by the trained classifier for the experimental evaluation, in accordance with some embodiments of the present invention. The graphs may help visually explain the process of excluding unreliable 3D volumes, for example, as described herein with reference to act 312. Narrow probability vectors (e.g., as shown in graphs 602A-C) are interpreted as reliable localizations, indicating 3D volumes that are retained. More spread and/or multi-peaked probability vectors (e.g., as shown in graphs 602D-F) are considered as less reliable, and the corresponding 3D volume may be rejected and/or excluded from further processing. Graphs 602D-F depict slices with considerable positioning errors and their corresponding class probabilities.

The RANSAC process was selected for the linear model, as described herein.

Figure 7A:
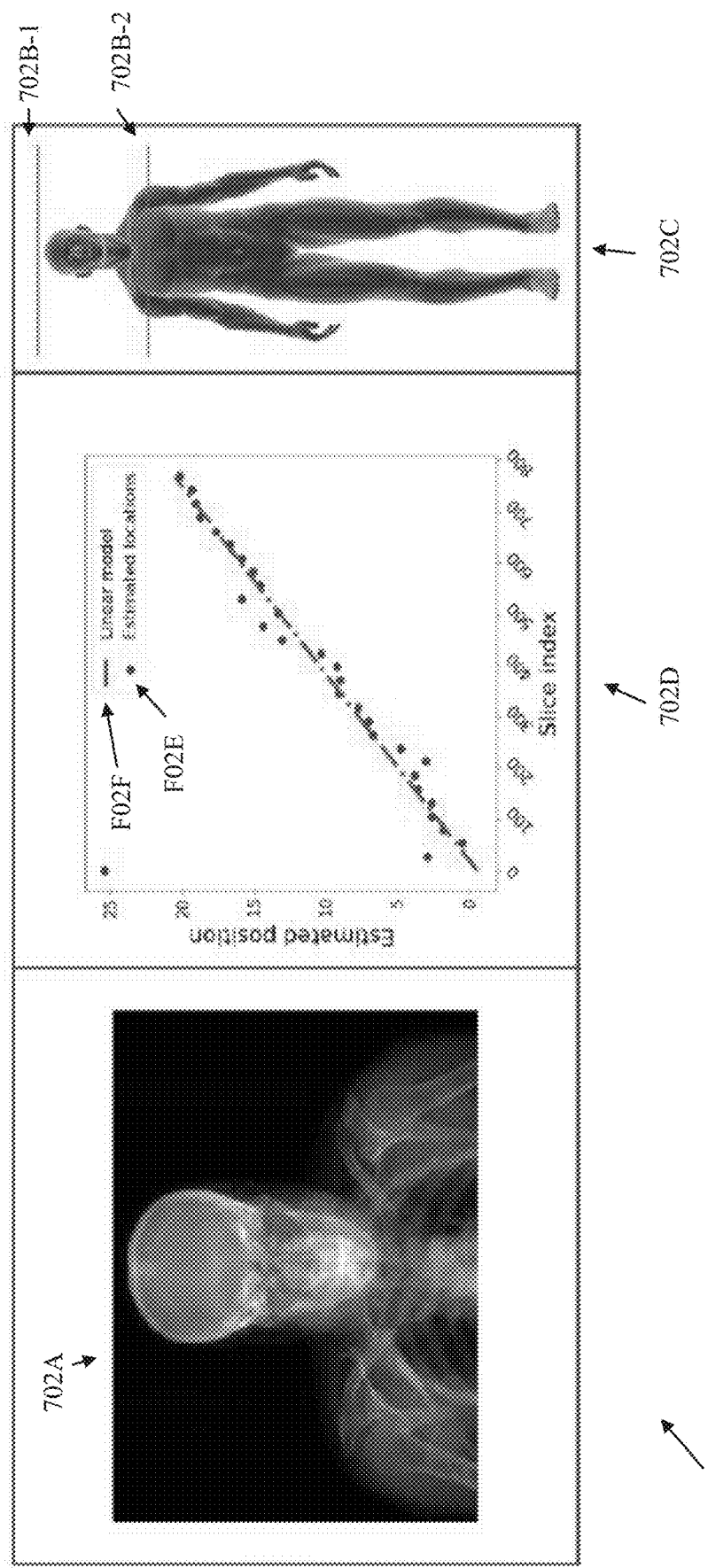
FIGS. 7A-C include several examples of CT scan, and a graph depicting corresponding localization of 30 equally spaced sampled slices fitted to a RANSAC based linear model for the experimental evaluation, in accordance with some embodiments of the present invention.
Figure 7B:
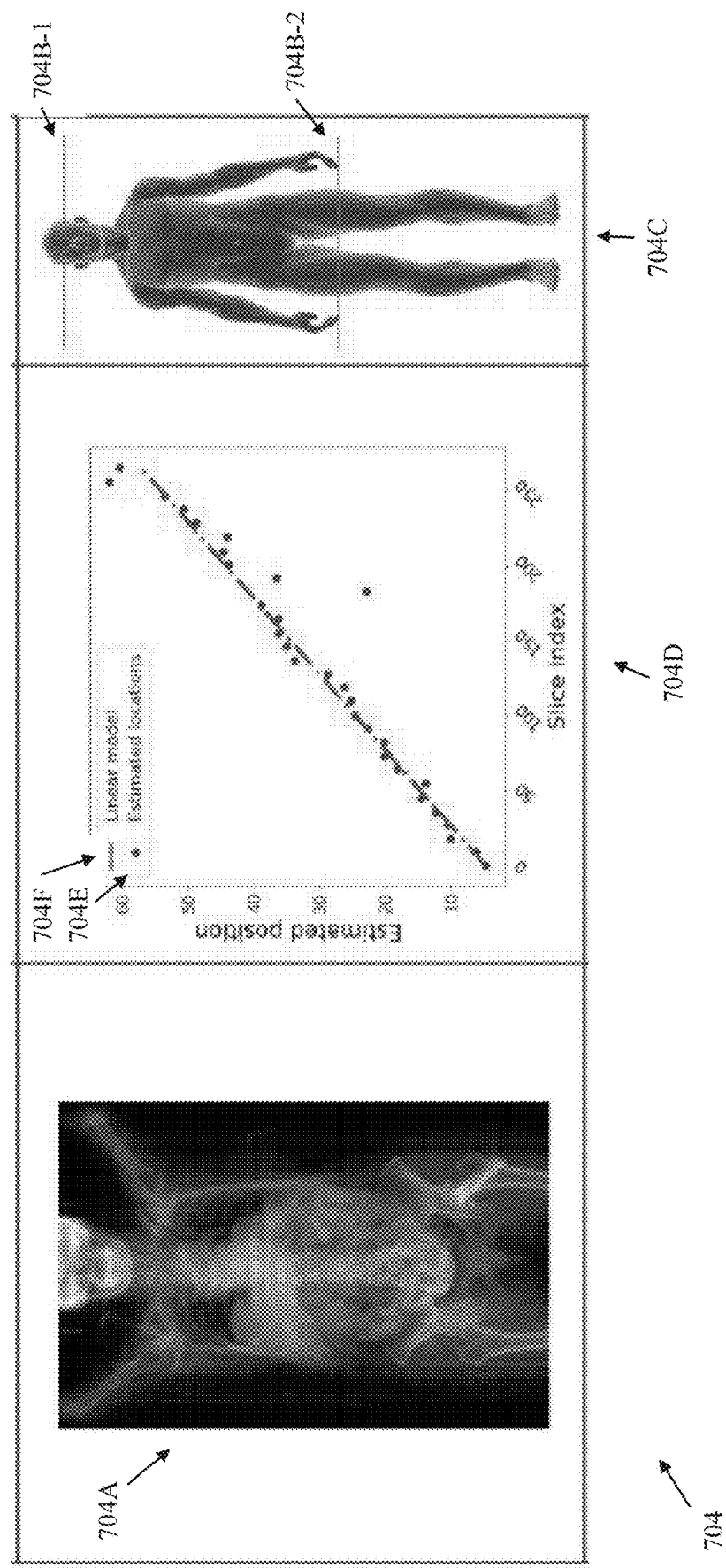
Figure 7C:
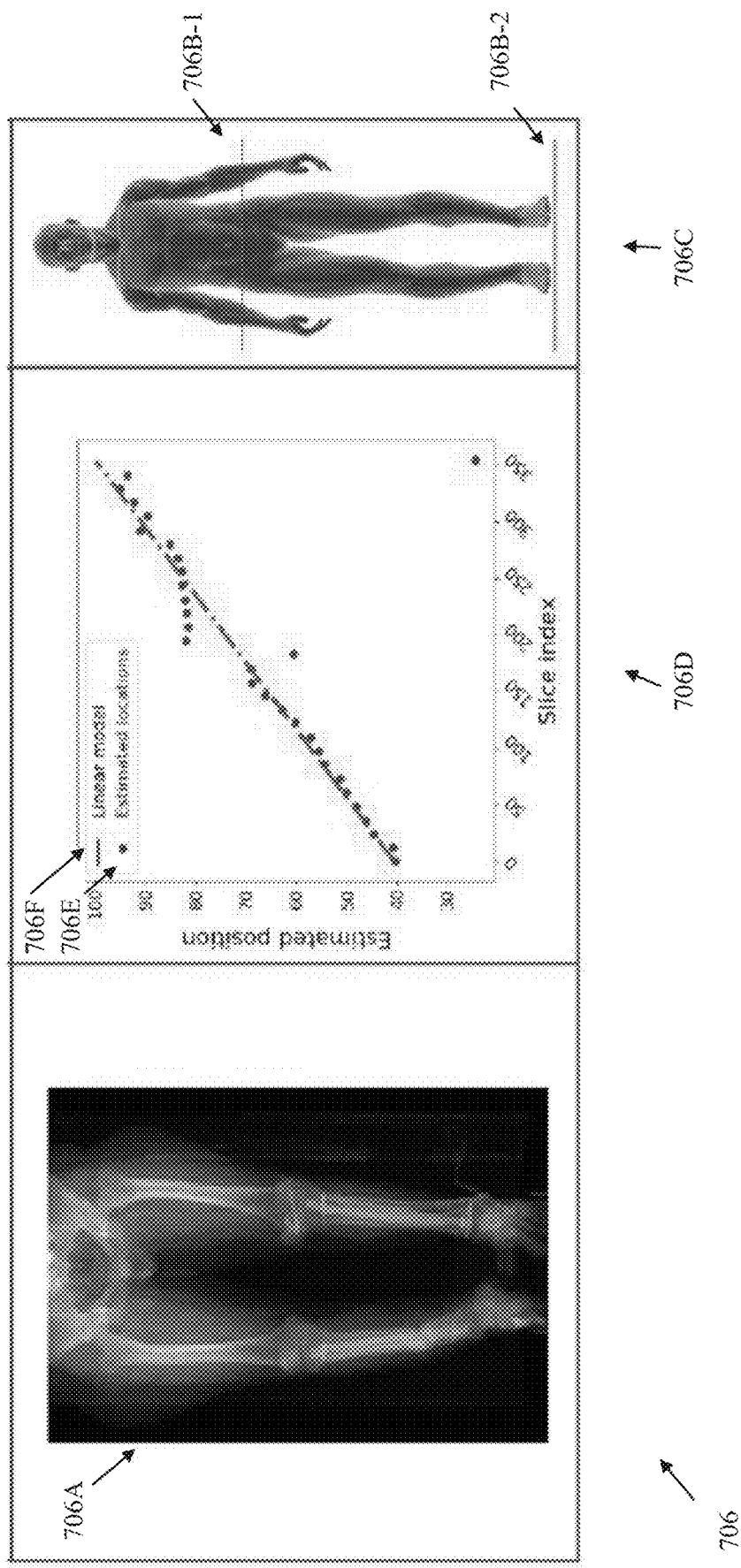

Reference is now made to FIGS. 7A-C, which include several examples of CT scan, and a graph depicting corresponding localization of 30 equally spaced sampled slices fitted to a RANSAC based linear model for the experimental evaluation, in accordance with some embodiments of the present invention.

Example 702 includes a summary CT volume 702A of a head region, which is represented between lines 702B-1 and 702B-2 of a body atlas 702C. Graph 702D is a plot of points 702E representing slice index versus estimated position computed by the classifier for the uniformly sampled slices. A straight line 702F represents a linear model fitted to the plotted points using the RANSAC approach.

Example 704 includes a summary CT volume 704A of a chest and abdomen region, which is represented between lines 704B-1 and 704B-2 of a body atlas 704C. Graph 704D is a plot of points 704E representing slice index versus estimated position computed by the classifier for the uniformly sampled slices. A straight line 704F represents a linear model fitted to the plotted points using the RANSAC approach.

Example 706 includes a summary CT volume 706A of a lower limbs region, which is represented between lines 706B-1 and 706B-2 of a body atlas 706C. Graph 706D is a plot of points 706E representing slice index versus estimated position computed by the classifier for the uniformly sampled slices. A straight line 706F represents a linear model fitted to the plotted points using the RANSAC approach.

It is noted that the outliers in graph 702D and graph 706D have no effect on the estimated linear model.

Inventors tested the accuracy of the localization process described herein based on a collection of 1500 CT scans of the chest-abdomen region. Those scans were processed by a vertebrae segmentation algorithm. The segmentation results were used to find the index of the distinct slices positioned in the middle point between T12-L1, L1-L2, L2-L3, L3-L4 and L4-L5 vertebrae centers. Following this procedure, Inventors generated 5 different collections, each collection composed of 1500 slices positioned at the same anatomical location. Those 1500 CT scans were also processed by the slice localization tool mapping every slice of every scan to the [0, 99] interval, based on at least some implementations of the systems, apparatus, methods, and/or code instructions described herein. Inventors calculated the mean and standard deviation of the localization values each slice in all 5 collections was assigned with.

Figure 8:
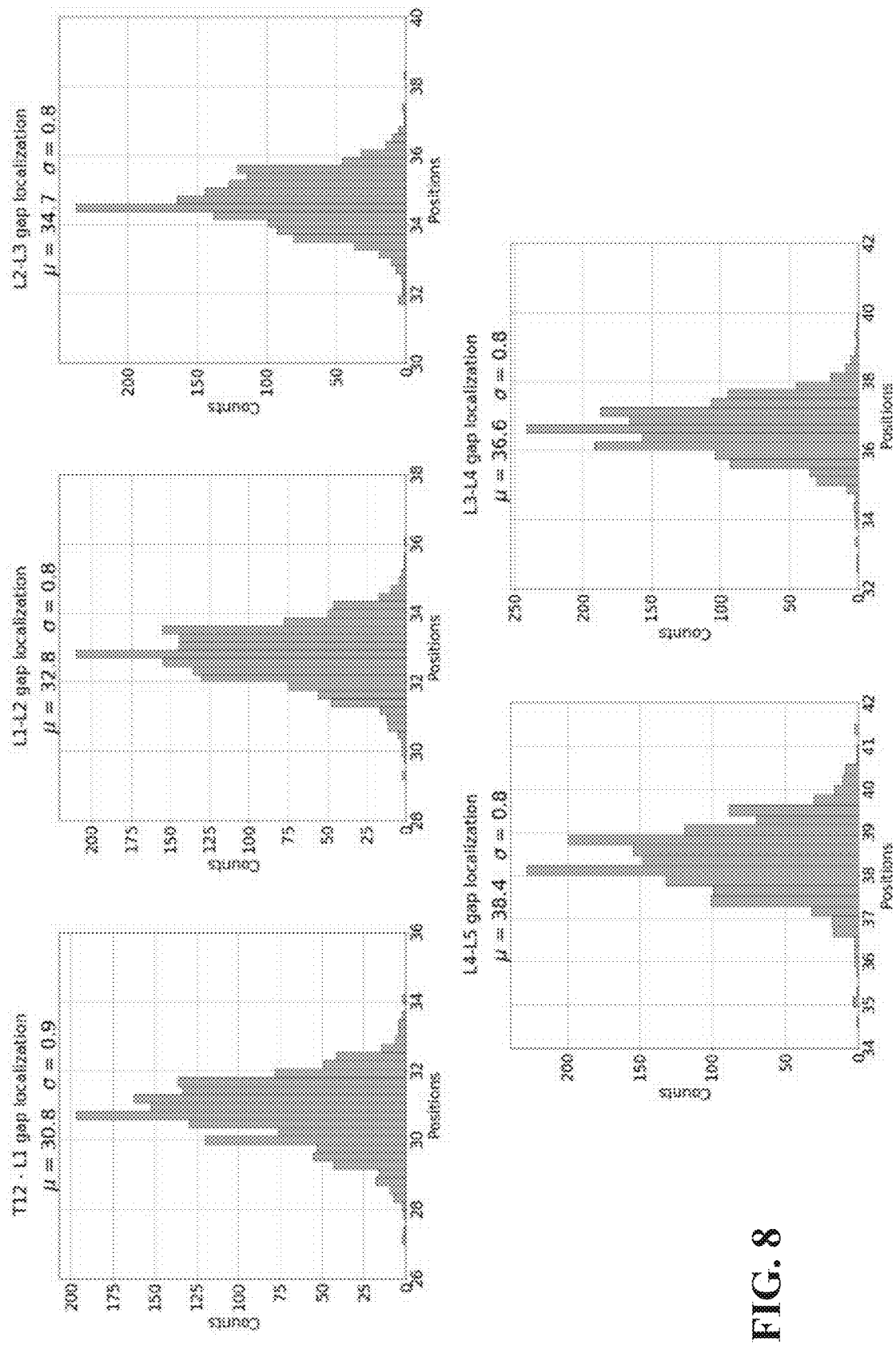
FIG. 8 is a set of histograms of the computed localization values for specific vertebra positions computed as part of the experimental evaluation, in accordance with some embodiments of the present invention.

Reference is now made to FIG. 8, which is a set of histograms of the computed localization values for specific vertebra positions computed as part of the experimental evaluation, in accordance with some embodiments of the present invention.

Since the entire human body is mapped to the [0, 99] interval and the average adult height is roughly 170 [cm], an error of one unit in the normalized scale is equivalent to about 1.7 centimeters. This means that for the evaluated anatomical ROIs, at least some of the systems, apparatus, methods, and/or code instructions described herein provides localization accuracy of about 1.5 centimeters.

The frontal projection and the corresponding localization results of 4000 scans of different body parts and protocols were plotted using the format shown in FIGS. 7A-C. The figures were inspected for locating the instances with inaccurate localizations. Using only the first 2000 scans, Inventors developed several rules which discriminate reliable from unreliable localizations. Those rules are based on the RANSAC fitting score and on the probability vectors of the subset of slices which were used for the model fitting. The created rules were tested on the remaining 2000 scans. The rules turned out to be very effective in filtering out unreliable scans. The analysis of the results show that 97.5% of the scans were rightfully classified as reliable (yield of 97.5%) and only a single scan was misclassified as reliable.

Once the exclusion criteria proved to be effective and reliable, the localization tool described herein was executed followed by the exclusion criteria on a larger collection of 21,500 unique scans of different body parts and protocols.

Figure 9:
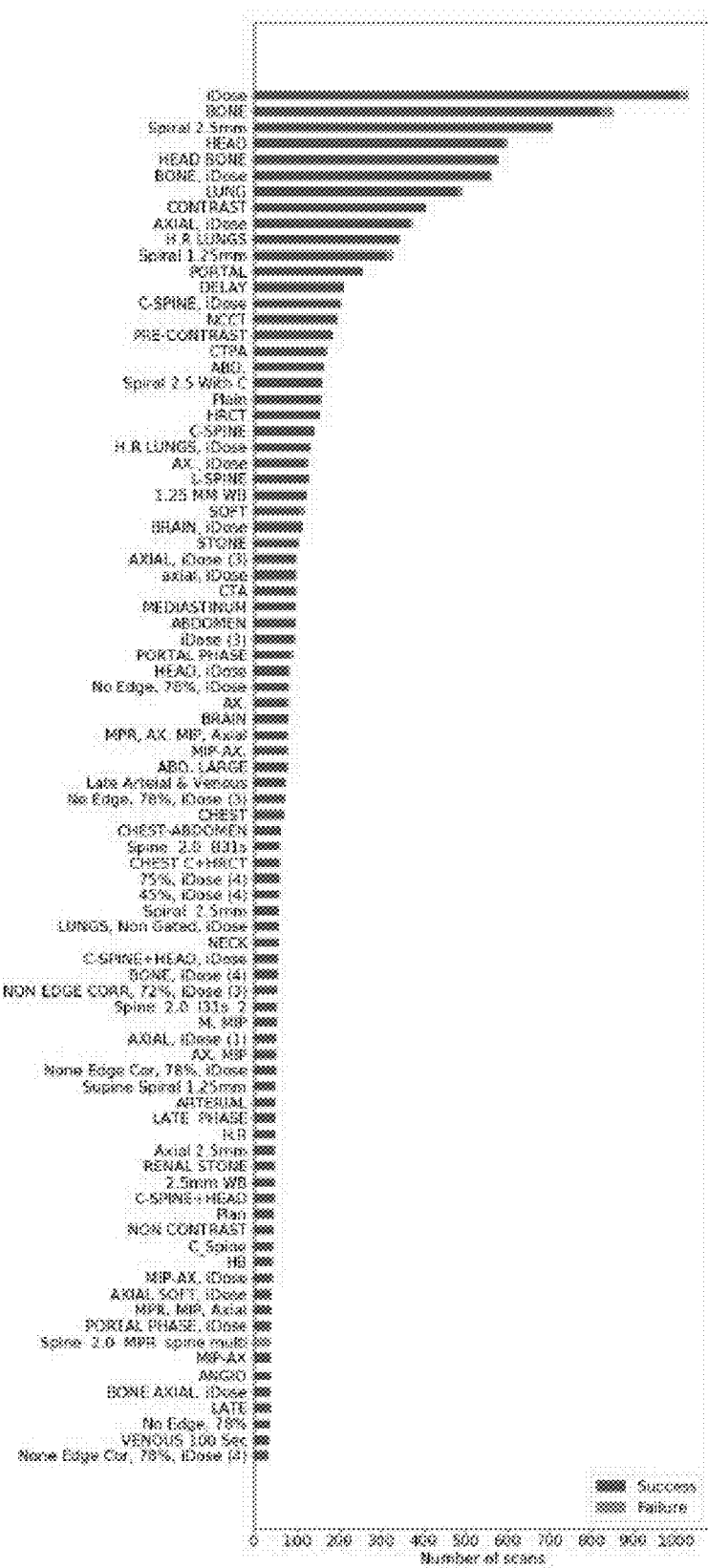
FIG. 9 is a plot of the success/failure ratio for the 60 most frequent series descriptions evaluated using the developed exclusion criteria of the computational evaluation, in accordance with some embodiments of the present invention.

Reference is now made to FIG. 9, which is a plot of the success/failure ratio for the 60 most frequent series descriptions evaluated using the developed exclusion criteria of the computational evaluation, in accordance with some embodiments of the present invention.

The descriptions of the various embodiments of the present invention have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

It is expected that during the life of a patent maturing from this application many relevant 3D volumes will be developed and the scope of the term 3D volume is intended to include all such new technologies a priori.

As used herein the term "about" refers to ±10%.

The terms "comprises", "comprising", "includes", "including", "having" and their conjugates mean "including but not limited to". This term encompasses the terms "consisting of" and "consisting essentially of".

The phrase "consisting essentially of" means that the composition or method may include additional ingredients and/or steps, but only if the additional ingredients and/or steps do not materially alter the basic and novel characteristics of the claimed composition or method.

As used herein, the singular form "a", "an" and "the" include plural references unless the context clearly dictates otherwise. For example, the term "a compound" or "at least one compound" may include a plurality of compounds, including mixtures thereof.

The word "exemplary" is used herein to mean "serving as an example, instance or illustration". Any embodiment described as "exemplary" is not necessarily to be construed as preferred or advantageous over other embodiments and/or to exclude the incorporation of features from other embodiments.

The word "optionally" is used herein to mean "is provided in some embodiments and not provided in other embodiments". Any particular embodiment of the invention may include a plurality of "optional" features unless such features conflict.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting. In addition, any priority document(s) of this application is/are hereby incorporated herein by reference in its/their entirety.

What is claimed is:

1. A computer implemented method for localizing target anatomical regions of interest (ROI) of a target individual, comprising:
uniformly sub-sampling a plurality of 2D images having sequential index numbers within a 3D anatomical volume;
feeding the plurality of sampled 2D images into a classifier for outputting a plurality of values on a normalized anatomical scale;
fitting a linear model to the plurality of values and corresponding sequential index numbers;
mapping by the linear model, the plurality of 2D images to the normalized anatomical scale;
receiving an indication of at least one target anatomical ROI of a target individual, wherein each target anatomical ROI is mapped to the normalized anatomical scale; and
providing a sub-set of the plurality of 2D images having values of the normalized anatomical scale corresponding to the received at least one target anatomical ROI.

2. The method of claim 1, further comprising planning a treatment of a patient according to an analysis of the respective sub-set of the plurality of 2D image having values corresponding to the certain target anatomical ROI.

3. The method of claim 1, further comprising executing a computer aided diagnosis (CAD) designed for analysis of a certain target anatomical ROI application, on the respective sub-set of the plurality of 2D image having values corresponding to the certain target anatomical ROI.

4. The method of claim 1, wherein the normalized anatomical scale comprises a one dimensional coordinate system of a plurality of equally spaced positions along an axial dimension of an arbitrary human body.

5. The method of claim 1, wherein the classifier classifies each of the plurality of sampled 2D images into at least one classification category of a plurality of classification categories, wherein the plurality of classification categories correspond to a number of equally spaced values along the normalized anatomical scale.

6. The method of claim 1, wherein the classifier computes a mapping confidence score indicative of confidence of the mapping between an inputted 2D image and the computed value, and rejecting the computed value when the mapping confidence score is according to a rejection requirement.

7. The method of claim 6, wherein the rejection requirement comprises a plurality of peak probability vectors for a single 2D image.

8. The method of claim 6, wherein the 2D image is retained when the mapping confidence score comprises a single and narrow probability vector.

9. The method of claim 1, wherein original pixel values of each of the sampled 2D images are inputted into the classifier.

10. The method of claim 1, wherein a total number of the plurality of 2D images is about 100-2000, wherein the uniformed sub-sampling is performed by selecting one 2D image for every about 10-50 sequential 2D images, and wherein a number of the sampled 2D images is about 20-50.

11. The method of claim 1, wherein the normalized anatomical scale is a continuous range of values ranging from 0 to 99, wherein a normalized position of a tip of a head is set to 0 and a lowest part of feet is set to 99.

12. The method of claim 1, wherein the 3D anatomical volume is a CT scan and the plurality of 2D images are axial slices of the CT scan.

13. The method of claim 1, wherein the plurality of 2D images are mapped to respective values of the normalized anatomical scale independently of DICOM® metadata associated with the 3D anatomical volume.

14. The method of claim 1, wherein the classifier is trained according to a training dataset of 3D anatomical volumes of a plurality of sample patients, where a plurality of 2D images of each 3D anatomical volume are labeled with value on a normalized anatomical scale computed by a process of: labeling each of a superior 2D image and an inferior 2D image with a value corresponding to a respective depicted defined anatomical landmark, labeling 2D images between the superior 2D image and the inferior 2D image with values computed by a linear interpolation of the values of the superior 2D image and inferior 2D image.

15. The method of claim 14, wherein the defined anatomical landmark and corresponding value are selected from the group consisting of: tip of head and 0, lateral ventricles and 10.9, hyoid bone and 12.6, superior sternum and 18.9, carina and 21.1, inferior heart and 28.0, $12^{th}$ rib ending and 36.6, superior pelvic bone and 40.0, lesser trochanter and 51.4, patella and 71.4, inferior feet and 100.0.

16. The method of claim 1, further comprising computing a fitting score for the fit of the linear model to the plurality of values and corresponding sequential index number of the respective sampled 2D image, wherein a fitting score requirement of the fitting score defines an error in the computation of the values, and rejecting the 3D anatomical volume when the fitting score meets a rejection requirement.

17. The method of claim 1, wherein the linear model is selected for fitting to noisy data with strong outliers.

18. The method of claim 17, wherein the linear model is based on the Random Sample Consensus (RANSAC) process.

19. The method of claim 1, further comprising evaluating the 3D anatomical volume for exclusion from further processing when a set of rules defining unreliable results is met, the set of rules based on a fitting score computed for the linear model and on probability vectors computed by the classifier for the sampled subset of 2D images.

20. A system for localizing target anatomical regions of interest (ROI) of a target individual, comprising:
at least one hardware processor executing a code for:
uniformly sub-sampling a plurality of 2D images having sequential index numbers within a 3D anatomical volume;
feeding the plurality of sampled 2D images into a classier for outputting a plurality of values on a normalized anatomical scale;
fitting a linear model to the plurality of values and corresponding sequential index numbers;
mapping by the linear model, the plurality of 2D images to the normalized anatomical scale;
receiving an indication of at least one target anatomical ROI of a target individual, wherein each target anatomical ROI is mapped to the normalized anatomical scale; and
providing a sub-set of the plurality of 2D images having values of the normalized anatomical scale corresponding to the received at least one target anatomical ROI.

21. A computer program product for localizing target anatomical regions of interest (ROI) of a target individual, comprising:
a non-transitory memory storing thereon code for execution by at least one hardware process, the code including instructions for:

uniformly sub-sampling a plurality of 2D images having sequential index numbers within a 3D anatomical volume;

feeding the plurality of sampled 2D images into a classifier for outputting a plurality of values on a normalized anatomical scale;

fitting a linear model to the plurality of values and corresponding sequential index numbers;

mapping by the linear model, the plurality of 2D images to the normalized anatomical scale;

receiving an indication of at least one target anatomical ROI of a target individual, wherein each target anatomical ROI is mapped to the normalized anatomical scale; and providing a sub-set of the plurality of 2D images having values of the normalized anatomical scale corresponding to the received at least one target anatomical ROI.

* * * * *